(12) United States Patent
Charlton et al.

(10) Patent No.: US 11,517,633 B2
(45) Date of Patent: Dec. 6, 2022

(54) PRODUCTION OF LU-177 AND OTHER RADIONUCLIDES VIA HOT ATOM CAPTURE ON NANOSTRUCTURED CARBON

(71) Applicant: Board of Regents, the University of Texas System, Austin, TX (US)

(72) Inventors: William S Charlton, Austin, TX (US); Donald D. Nolting, Austin, TX (US); Adam J. Samia, Austin, TX (US); Joseph Lapka, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/555,839

(22) Filed: Dec. 20, 2021

(65) Prior Publication Data
US 2022/0193276 A1 Jun. 23, 2022

Related U.S. Application Data

(60) Provisional application No. 63/288,890, filed on Dec. 13, 2021, provisional application No. 63/278,979, (Continued)

(51) Int. Cl.
*A61K 51/12* (2006.01)
*C01B 32/159* (2017.01)
(Continued)

(52) U.S. Cl.
CPC ...... *A61K 51/1268* (2013.01); *A61K 51/1217* (2013.01); *C01B 32/159* (2017.08); (Continued)

(58) Field of Classification Search
CPC ............ A61K 51/1268; A61K 51/1217; C01B 32/159; C01B 32/174; C01B 32/198; (Continued)

(56) References Cited

U.S. PATENT DOCUMENTS

| | | | |
|---|---|---|---|
| 6,222,896 B1 | 4/2001 | Jia et al. | |
| 8,540,965 B2* | 9/2013 | Scheinberg | A61K 47/6925 424/9.34 |
| 2013/0170593 A1* | 7/2013 | Jansen | G21G 1/06 376/158 |

FOREIGN PATENT DOCUMENTS

WO 2011-111010 A1 9/2011

OTHER PUBLICATIONS

Lu, et al., Adsorption and desorption of radionuclide europium(III) on multiwalled carbon nanotubes sturdied by batch techniques, J. Radioanal. Nucl. Chem. 2011; 287: 893-898 (Year: 2011).*

(Continued)

*Primary Examiner* — Daniel C. McCracken
(74) *Attorney, Agent, or Firm* — Kilpatrick Townsend & Stockton LLP

(57) ABSTRACT

Described are methods for preparing radionuclides, such as radionuclides having a high specific activity. The disclosed methods include irradiating target nuclide materials, in solution, with a neutron source. The radionuclides can be separated from the target nuclide material by providing a solid carbon nanostructured material, as a suspension of solids, proximal to the target nuclide material in solution and using the recoil to drive adsorption of the radionuclide onto the solid carbon nanostructured material to transfer the radionuclides from the liquid phase (in solution) to the solid phase (adsorbed to the suspended solid carbon nanostructured material). One or more surfactants can be incorporated into the solution to facilitate formation of a stable suspension of the solid carbon nanostructured material.

20 Claims, 9 Drawing Sheets

Related U.S. Application Data filed on Nov. 12, 2021, provisional application No. 63/128,609, filed on Dec. 21, 2020.

(51) Int. Cl.

| | | |
|---|---|---|
| *C01B 32/174* | (2017.01) | |
| *C01B 32/198* | (2017.01) | |
| *G21G 1/06* | (2006.01) | |
| *B82Y 5/00* | (2011.01) | |
| *B82Y 40/00* | (2011.01) | |
| *G21G 1/00* | (2006.01) | |

(52) U.S. Cl.
CPC .......... *C01B 32/174* (2017.08); *C01B 32/198* (2017.08); *G21G 1/06* (2013.01); *B82Y 5/00* (2013.01); *B82Y 40/00* (2013.01); *C01B 2202/02* (2013.01); *C01P 2004/03* (2013.01); *C01P 2006/88* (2013.01); *G21G 2001/0036* (2013.01); *G21G 2001/0094* (2013.01)

(58) Field of Classification Search
CPC ................... C01B 2202/02; G21G 1/06; G21G 2001/0036; G21G 2001/0094; B82Y 5/00; B82Y 40/00; C01P 2004/03; C01P 2006/88

See application file for complete search history.

(56) References Cited

OTHER PUBLICATIONS

Bandyopadhyaya, et al., Stabilization of Individual Carbon Nanotubes in Aqueous Solutions, Nano Letters 2002; 2(1): 25-28 (Year: 2002).*

Sanginario, et al., Carbon Nanotubes as an Effective Opportunity for Cancer Diagnosis and Treatment, Biosensors 2017; 7(9): pp. 1-23 (Year: 2017).*

Fishman, et al., The Szilard-Chalmers Reaction in Aqueous Solutions of Tri- and Hexavalent Chromium, J. Chem. Phys. 1954; 22: 1088-1093 (Year: 1954).*

Bandyopadhyaya, et al., Stabilization of Individual Carbon Nanotubes in Aqueous Solutions. Nano Letters, 2002, 2(1), 25-28.

Dash, A, Production of I77Lu for Targeted Radionuclide Therapy: Available Options. Nucl. Med. Mol. Imaging, 2015, 49, 85-107.

Deb, et. al., Carbon Nano Tubes Functionalized with Novel Functional Group Amido-Amine for Sorption of Actinides. J. Hazardous Materials, 2018, 345, 63-75.

Fan, et. al., Adsorption of Humic Acid and Eu(III) to Multi-Walled Carbon Nanotubes: Effect of pH, Ionic Strength and Counterion Effect. Radiochim Acta, 2009, 97, 141-148.

Harbottle, G., Chemical Effects of Nuclear Transformations in Inorganic Solids. Annu. Rev. Nucl. Sci., 1965, 15, 89-124.

Horowitz, et. al., A Process for the Separation of I77Lu from Neutron Irradiated I76Yb Targets. Appl. Radiat. Isot., 2005, 63(1), 23-36.

Lin, et. al., Enrichment of Copper-64 by the Szilard Chalmers Process. J. Nucl. Sci. Technol., 1966, 3(7), 289-293.

Ramasamy, et. al., Fabrication of Carbon Nanotubes Reinforced Silica Composites with Improved Rare Earth Elements Adsorption Performance. Chem. Eng. Journal, 2019, 365, 291-304.

Safavi-Tehrani, et. al., Production of High Specific Activity Radiolanthanides for Medical Purposes Using the UC Irvine TRIGA Reactor. J. Radioanal. Nucl. Chem., 2015, 303, 1099-1103.

Sharaf El-Deen, et. al., Evaluation of CNTs/Mn02 Composite for Adsorption of 60Co(II), 65Zn(II) and Cd(II) Ions from Aqueous Solutions. Radiochim. Acta, 2017, 105(1), 43-55.

Szilard, et. al., Chemical Separation of the Radioactive Element from its Bombarded Isotope in the Fermi Effect. Nature, 1934, 134, 462.

Tan, et. al., Adsorption and Kinetic Desorption Study of 152+ 154 Eu(III) on Multiwall Carbon Nanotubes from Aqueous Solution by Using Chelating Resin and XPS Methods. Radiochimica Acta., 2008, 96, 23-29.

Van Dorp, et. al., Towards the Production of Carrier-Free 99Mo by Neutron Activation of 98Mo in Molybdenum Hexacarbonyl-Szilard-Chalmers Enrichment. Appl. Radiat. Isot., 2018, 140, 13 8-145.

Wang, et. al., Sorption of 243Am(III) to Multiwall Carbon Nanotubes. Environ. Sci. Technol., 2005, 39, 2856-2860.

Wang, et. al., Different Interaction Mechanisms of Eu(III) and 243Am(III) with Carbon Nanotubes Studied by Batch, Spectroscopy Technique and Theoretical Calculation. Environ. Sci. Technol., 2015, 49, 11721-11728.

Application No. PCT/US2021/064306, International Search Report and Written Opinion, dated May 16, 2022, 16 pages.

* cited by examiner

PRODUCTION OF LU-177 AND OTHER RADIONUCLIDES VIA HOT ATOM CAPTURE ON NANOSTRUCTURED CARBON

CROSS-REFERENCE TO RELATED APPLICATIONS

This application claims the benefit of and priority to U.S. Provisional Application No. 63/128,609, filed on Dec. 21, 2020, 63/278,979, filed on Nov. 12, 2021, and 63/288,890, filed on Dec. 13, 2021, which are hereby incorporated by reference in their entireties.

FIELD

This invention is in the field of radionuclide preparation. This invention relates generally to techniques for the preparation of radionuclides via liquid/solid hot atom capture.

BACKGROUND

Lu-177 is a radioactive isotope in high demand as a therapeutic for the treatment of several types of cancer and may have other nuclear medicine applications. Conventionally, Lu-177 can be produced by irradiation of enriched Yb in a nuclear reactor, followed by a difficult chemical separation of the Lu-177 from the remaining Yb, with low yields. The enriched Yb can then be recycled back into the reactor for further production. Current methods for production require large Yb targets, costly chemical resins, potentially significant losses of both the Lu-177 (due to decay in the columns) and the unirradiated Yb, and can produce large volumes of radioactive waste. Most of these drawbacks are due to the extremely dilute (1-10 ppm) quantity of Lu-177 following irradiation.

SUMMARY

In an aspect, this disclosure relates to methods of producing medical radioisotopes using neutron irradiation of a target material that transfers the radioactivated products during irradiation from a liquid to a solid state for efficient post-irradiation separation. Aspects of the disclosed methods are based on the Szilard-Chalmers effect (discovered in 1934), which shows that during neutron activation (and subsequent emission of a gamma-ray), the activated atom recoils from the reaction with sufficient kinetic energy (typically 100-1000 eV) to rupture the chemical bonds holding the activated nucleus in its compound and leaving the activated nucleus in a different oxidation state from the non-activated target material. However, the disclosed methods are distinct from previously developed methods using the Szilard-Chalmers effect. For example, the methods described herein can involve capture of the radioactivated product on a carbon nanostructured adsorber immediately during irradiation. As another example, the disclosed methods can employ a liquid target material solution combined with a solid carbon nanostructured adsorber to transfer the radioactivated product from the liquid state to the solid state instead of solid-solid transfer used in typical Szilard-Chalmers configurations. As a further example, the carbon nanostructured adsorber can be in a suspension that provides a minimal separation between the target material molecules and the adsorber structures that is suitable to enhance capture of the activated nucleus and suppress annealing of the radioactivated product back into the original liquid target.

In some examples, methods of this aspect may comprise obtaining a target aqueous suspension and irradiating the target aqueous suspension with a neutron source. For example, at least some of the target nuclide material may absorb neutrons from the neutron source to generate radionuclides that recoil and are adsorbed by the solid carbon nanostructured material to form loaded solid carbon nanostructured material in the suspension. In some examples, the target aqueous suspension comprises a solid carbon nanostructured material, water, a surfactant, and a target nuclide material. In some embodiments, the invention may comprise a method comprising: irradiating a target aqueous suspension with a neutron source, wherein at least some of a target nuclide material absorbs neutrons from the neutron source to generate radionuclides that recoil and are adsorbed by a solid carbon nanostructured material to form loaded solid carbon nanostructured material, and wherein the target aqueous suspension comprises: the solid carbon nanostructured material; water; a surfactant; and the target nuclide material. In some embodiments, the invention may comprise the target aqueous solution.

In some embodiments, the aqueous suspension may comprise metal salts including, but not limited to, nitrates, sulfates, or phosphates with the metal selected from the group of metals in the Periodic Table of the Elements from scandium (Sc), with atomic number of 21, to bismuth (Bi), with an atomic number of 83, e.g., excluding the noble elements of krypton (Kr) and xenon (Xe). The target nuclide may be in an aqueous form to be compatible with the suspended adsorber (solid carbon nanostructured material) and to maximize radionuclide transfer to the solid adsorber.

The solid adsorber may comprise a solid carbon nanostructured material such as single walled carbon nanotubes (SWCNT), multiwalled carbon nanotubes (MWCNT), carbon nanohorns, carbon nanocones, carbon nanoribbons, layered graphitic sheets, C60 (buckminsterfullerene), or any other fullerene or derivate of a buckminsterfullerene (C20, C70, C72, C76, C84, C100, carbon nano-onion, etc.). The SWCNT or MWCNTs may be pristine, functionalized, or modified. The carbon nanostructured adsorber may advantageously be resistant to radiological decomposition during irradiation. The carbon nanostructured adsorbers may be suspended using a surfactant, such as a polysaccharide surfactant, which may include gum arabic (GA) (a hydrocolloid that provides stability to oil-in-water emulsions, and is a mixture of glycoproteins and polysaccharides, usually predominantly arabinose and galactose, such that in addition to or instead of GA, the invention can be practiced with a glycoprotein(s) and polysaccharide(s) mixture that has surfactant or stabilizing properties akin to GA), or chitosan, a cationic biopolymer. The surfactant may also be derived from proteins such as collagen. Surfactants are also dispersants, and vice versa, i.e., the art considers that surfactants can act as detergents, wetting agents, emulsifiers, foaming agents or dispersant, and that a dispersant or dispersing agent or dispersion aid can be a surfactant. In the context of the present invention, surfactants that act as surface active agents, emulsifiers, dispersants or detergents are advantageous, appreciating that there can be overlap as to these terms, e.g., a dispersant or emulsifier or surface active agent can be a detergent; a surface active agent can be a dispersant or emulsifier or detergent, etc. Thus, in some examples the surfactant can comprise a dispersing agent or dispersant or dispersion aid. In some examples, the surfactant may comprise graphene oxide. Graphene oxide may be considered a dispersant or dispersing agent or dispersion aid type of surfactant that can be used in the practice of the invention. Addition of graphene oxide to a solution in the practice of the invention, without wishing to be bound by any one particular theory, may function in the same way to disperse the solid carbon nanostructured material as other surfactants, like gum arabic. For example, both gum arabic and graphene oxide can serve as dispersion aid or dispersant or dispersing agent type surfactants by providing and maintaining a physical spacing between individual solid carbon nanostructured objects or molecules or groups of solid carbon nanostructured materials, which can allow for long-range ordering of the solid carbon nanostructured materials in an aqueous suspension. Accordingly, the surfactants useful in the practice of the invention typically comprise an agent or agents that improve separation of particles, and can be any type of surfactant, including, advantageously, agents that are considered in the art to be surface acting agents or surfactants, or detergents, or emulsifying agents, or emulsifiers, or dispersants, or dispersion aids, or dispersing agents. The surfactant may be resistant to radiological decomposition during irradiation. The adsorber materials may be evenly distributed in the suspension by centrifugation, sonification, and/or vigorous stirring. Such an even distribution may be beneficial because the recoil nucleus from the Szilard-Chalmers effect may only have a small range in the liquid target material.

The combined suspension of the liquid target solution and carbon nanostructured adsorber can be inserted into a metal, glass, or plastic container and exposed to a neutron irradiation field to produce the desired activated product and transfer that product to the solid adsorber. In embodiments, the length of this irradiation may be less than or about 1 hour and as up to or about 10 days, for example.

Methods of this aspect may further comprise separating the loaded solid carbon nanostructured material from a liquid phase of the suspension; and treating the loaded solid carbon nanostructured material with adsorbed radionuclides with an acid to release the radionuclides to solution. For example, following irradiation, the non-activated, liquid target solution can be physically separated from the solid adsorber and then the radioactivated product (e.g., medical radioisotopes) can be removed from the adsorber through washing with a solution of either a mineral acid, organic acid, or a complexant such as hydrochloric acid, nitric acid, sulfuric acid, ascorbic acid, acetic acid, oxalic acid, citric acid, or polyaminocarboxylates (such as EDTA, DOTA, or DTPA).

The resultant solution containing radionuclides (e.g., medical isotopes) may be or represent a concentrated form of the radionuclides, such as exhibiting a high specific activity. For example, a ratio of the radionuclides of the atom to stable or longer-lived nuclides of the atom in the concentrated form may be from 0.1 to 800. In some examples, the concentrated form may have a specific activity from 50 GBq/mg to 9000 GBq/mg.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION

Figure 1:
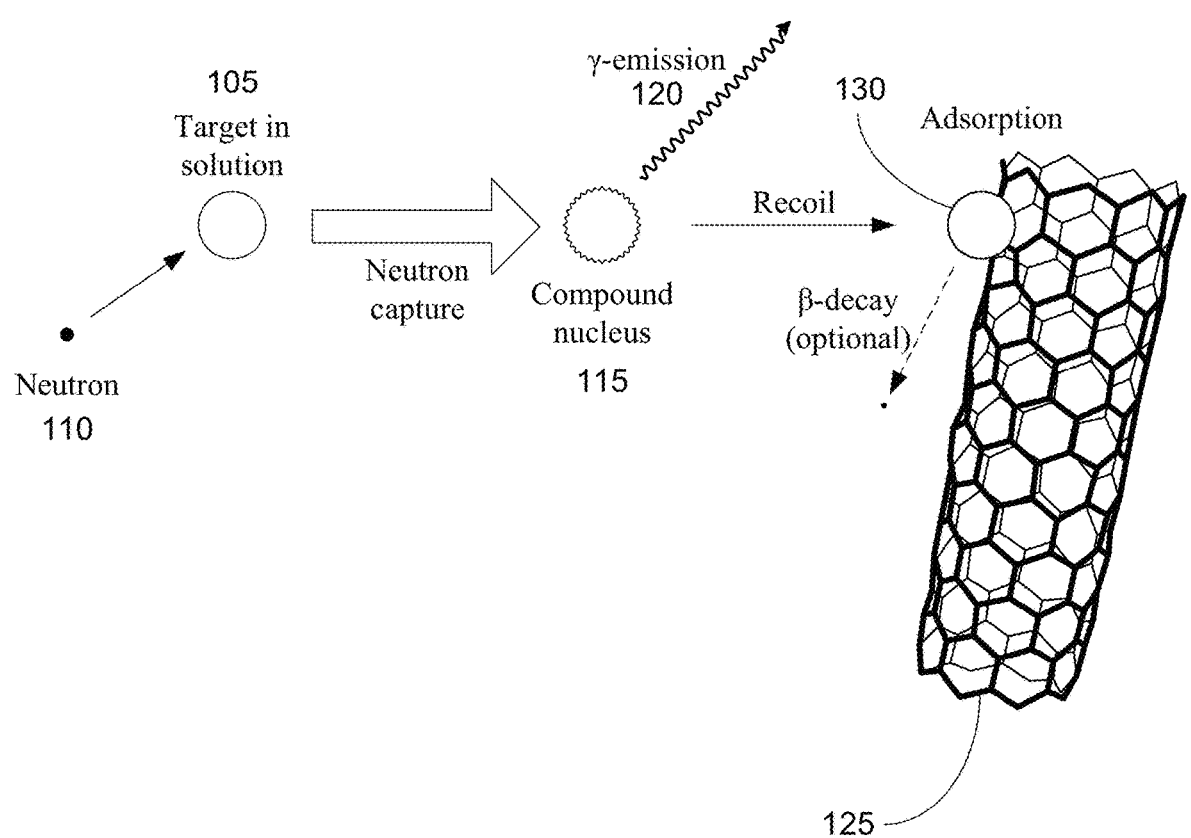
FIG. 1 provides a schematic illustration of preparation and adsorption of a radionuclide on a solid carbon nanostructured material.

Described herein are methods for preparing radionuclides, such as radionuclides having a high specific activity. The disclosed methods employ aspects of the Szilard-Chalmers effect, where target nuclide materials are irradiated with a neutron source to convert the target nuclide materials to radionuclides that recoil upon absorbing a neutron and emission of gamma radiation. The radionuclides can be separated from the target nuclide material by providing a solid carbon nanostructured material proximal to the target nuclide material and using the kinetic energy of the recoil to drive adsorption of the radionuclide onto the solid carbon nanostructured material. By placing the target nuclide material in a solution containing the solid carbon nanostructured material as a suspension, emulsion, colloid, or other dispersion, the radionuclides can be physically shifted from the liquid phase (in solution) to the solid phase (adsorbed to the suspended solid carbon nanostructured material), which can allow for efficient and effective separation of the radionuclides from the target nuclide materials. One or more surfactants can be incorporated into the solution to facilitate formation of a stable suspension of the solid carbon nanostructured material. The solid carbon nanostructured material loaded with adsorbed radioisotopes can be separated from the solution containing the target nuclide material, such as by a simple filtration or centrifugation process, allowing the target nuclide material to be recycled for further neutron irradiation for production of radioisotopes. The separated solid carbon nanostructured material loaded with adsorbed radioisotopes can be subjected to a release agent, such as an acid, to release the adsorbed radioisotopes to solution, which can then be separated from the solid carbon nanostructured material (e.g., by filtration or centrifugation), and used or purified further.

The disclosed methods can allow for efficient production of high-purity or high specific activity radioisotopes. This can be achieved because the target nuclide material can remain in solution, whereas the radioisotopes can be adsorbed to the solid carbon nanostructured material and easily separated. In this way, low (e.g., none) or only trace amounts of the target nuclide material can be present in or with the purified radioisotopes released from the solid carbon nanostructured material.

In general, the terms and phrases used herein have their art-recognized meaning, which can be found by reference to standard texts, journal references and contexts known to those skilled in the art. The following definitions are provided to clarify their specific use in the context of the invention.

"Target nuclide," "target nuclide material", or "target" refer to an atomic isotope or compound containing an atomic isotope for which neutron capture is desired to convert the atomic isotope to a different, usually radioactive, isotope, sometimes referred to as a "radionuclide." The radionuclide may be a radioactive isotope, which can undergo radioactive decay, sometimes quickly converting the radionuclide to another radionuclide species of a different atomic number (e.g., daughter radionuclide or product radionuclide). For example, in some cases, the initial radionuclide generated upon capture of a neutron and recoil and/or release of gamma radiation may undergo radioactive decay with a short half-life, such as a few seconds or a few hours, and the resultant daughter nuclides may be the ultimate radionuclide of interest (product radionuclide). In some cases, a radionuclide can undergo prompt relaxation to a lower energy configuration, such as by emitting gamma radiation. The radionuclides (optionally including daughter radionuclides or product radionuclides) may be useful, in embodiments, in nuclear medicine. In some cases, the radionuclides may have half-lives ranging from a few hours to a few weeks.

"Solid carbon nanostructured material" refers to an allotrope of carbon characterized by molecules or structures having at least one dimension of between 1 nm and 1 μm, such as a length, width, height, diameter, etc. and being in the solid state (i.e., not in the liquid state or in a dissolved state). As used herein, solid carbon nanostructured material includes carbon allotropes in which at least some, or optionally a majority or all, of the carbon atoms in the molecule or structure exhibit sp2 hybridization. Examples of solid carbon nanostructured materials include, but are not limited to, carbon nanotubes (e.g., singled-walled or multi-walled carbon nanotubes), graphene, graphitic sheets, carbon nanohorns, or fullerenes (e.g., C60, C70, etc.). In some cases, amorphous carbon, carbon black, and other forms of atomic carbon may not be considered solid carbon nanostructured materials. Solid carbon nanostructured materials may be pristine (e.g., free of non-carbon or non-hydrogen substituents, defects, or dopants), functionalized (e.g., contain non-carbon or non-hydrogen substituents), or modified (e.g., include non-carbon dopants, such as metal atoms or ions, or include structural defects). Solid carbon nanostructured material may be dispersed in a liquid, where particles or agglomerates of the solid carbon nanostructured material may be suspended in a liquid, such as in the form of a colloid or suspension.

"Resistant to radiological decomposition" refers to a property of a material, composition, molecule, or other species indicating that the material, composition, molecule, or other species does not undergo significant decomposition, degradation, or other physical or chemical change upon exposure to nuclear radiation, such as from a nuclear reactor (e.g., neutrons, gamma radiation, alpha particles, beta particles, etc.), for a period of time. Stated another way, a material, composition, molecule, or other species that is resistant to radiological decomposition may be stable for the duration of an exposure to nuclear radiation, such as from a nuclear reactor, during which target nuclides interact with neutrons in the nuclear radiation, such that its physical or chemical properties do not significantly change during the duration of the exposure.

FIG. 1 provides a schematic illustration of aspects of the disclosed methods for generating radionuclides. As illustrated, a target nuclide 105, present in solution, such as in the form of a cation (e.g., metal cation) or in a molecular anion (e.g., an oxyanion, like perrhenate ion), is exposed to neutrons 110. When a neutron 110 is captured by the target nuclide 105, a compound nucleus 115 is generated, which can have a mass number greater by 1 than the target nuclide. The compound nucleus 115 can have excess energy, which is released by emission of a gamma ray 120 and recoil of the resultant radionuclide 130 as a hot atom. With a solid carbon nanostructured material 125 proximal to the target nuclide 105 and/or compound nucleus 115, the resultant hot atom radionuclide 130 can be adsorbed to the solid carbon nanostructured material 125. In some cases, the adsorbed radionuclide 130 can undergo further radioactive decay (e.g., $\beta^-$ emission) to generate a product radionuclide adsorbed to the solid carbon nanostructured material 125.

The target nuclide 105 can be any suitable nuclide, such as any element having an atomic number from 21 to 83. Advantageous nuclides include elements of the lanthanide series, elements of the platinum group metals (PGMs), such as rhodium, ruthenium, iridium and osmium, rare earth elements, or various transition metals (e.g., first row, second row or third row transition metals), e.g., Yb, Lu, Re, Gd, TB, Mo, Tc, Ho, Dy, Ir, Sn, Y, Pd, or Cr. In some specific examples, the target nuclide 105 is a Yb-176 salt, a Re-185 salt, a perrhenate salt of Re-185, a Gd-160 salt, a Mo-98 salt, a Ho-165 salt, a Dy-164 salt, a Ir-191 salt, a Sn-116 salt, a Y-89 salt, a Pd-102 salt, or a Cr-50 salt, and the radionuclide or product radionuclide is Yb-177, Lu-177, Re-186, Gd-161, Tb-161, Mo-99, Tc-99m, Ho-166, Dy-165, Dy-166, Ir-192, Sn-117m, Y-90, Pd-103 or Cr-51. In some specific examples, the solid carbon nanostructured material comprises carbon nanotubes, single walled carbon nanotubes, multiwalled carbon nanotubes, carbon nanohorns, layered graphitic sheets, one or more fullerenes, or graphene.

Figure 2:
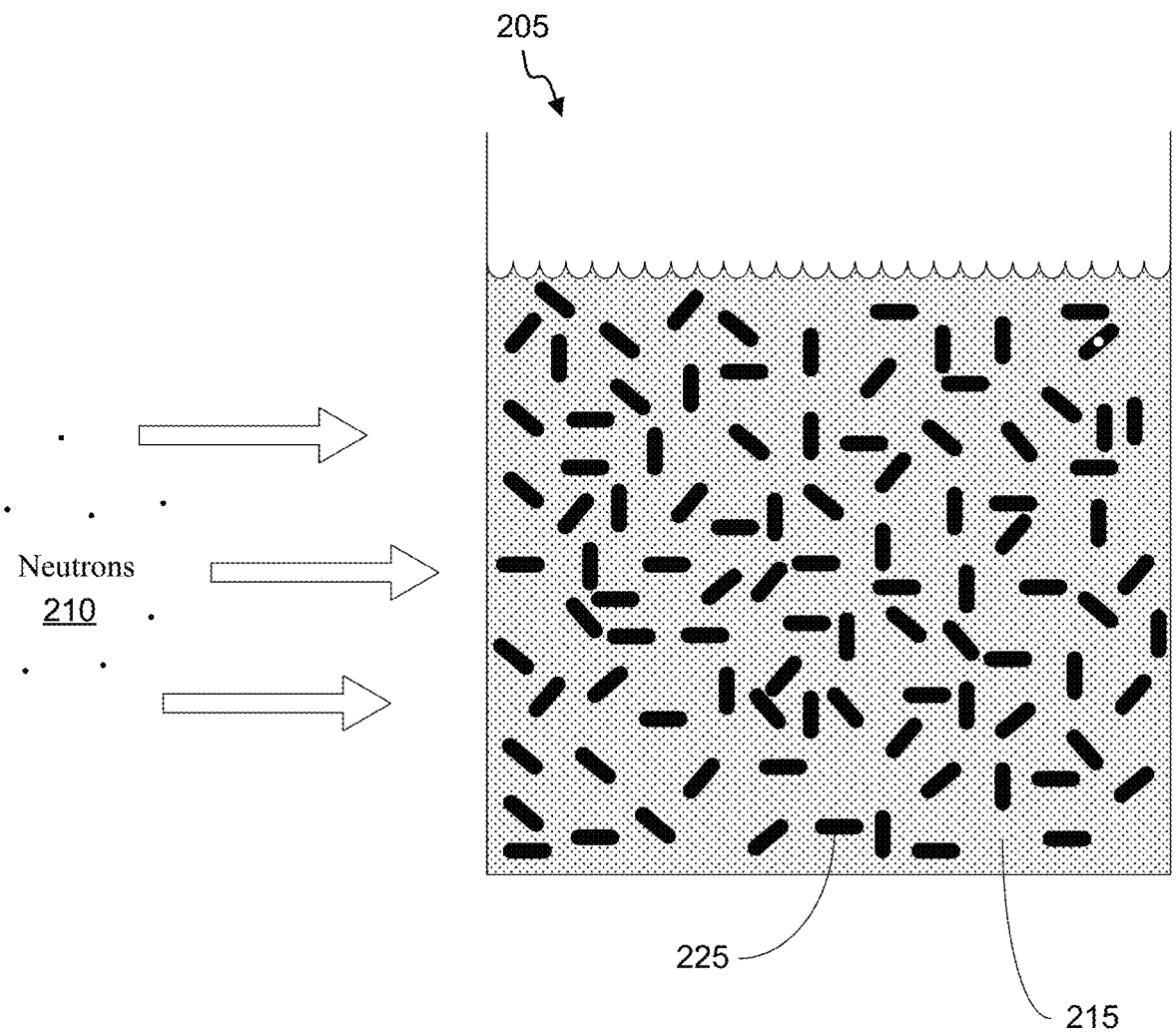
FIG. 2 provides a schematic illustration of exposure of a target solution with suspended solid carbon nanostructured material to a neutron source.

This configuration can occur in bulk to generate quantities of the radionuclide or product radionuclide. For example, as illustrated in FIG. 2, a sample of a target aqueous suspension 205 can be irradiated by neutrons 210 from a neutron source. The neutron source can be, for example, a core of a nuclear reactor, though other neutron sources can be used, such as particle accelerators, fissile nuclear material, etc. The time duration for irradiation by neutrons 210 can be any suitable time duration. In some embodiments, for example, the time duration may be as short as tens of minutes or as long as several weeks, such as from 10 minutes to 60 minutes, from 60 minutes to 6 hours, from 6 hours to 24 hours, from 1 day to 2 days, from 2 days to 5 days, from 5 days to 10 days, or from 10 days to 30 days. In some embodiments, the fluence of neutrons delivered to the sample from the neutron source may be as low as $1 \times 10^{13}$ neutrons/cm$^2$ or as high as $1 \times 10^{20}$ neutrons/cm$^2$, such as from $1 \times 10^{13}$ neutrons/cm$^2$ to $1 \times 10^{14}$ neutrons/cm$^2$, from $1\times10^{14}$ neutrons/cm$^2$ to $1\times10^{15}$ neutrons/cm$^2$, from $1\times10^{15}$ neutrons/cm$^2$ to $1\times10^{16}$ neutrons/cm$^2$, from $1\times10^{16}$ neutrons/cm$^2$ to $1\times10^{17}$ neutrons/cm$^2$, from $1\times10^{17}$ neutrons/cm$^2$ to $1\times10^{18}$ neutrons/cm$^2$, from $1\times10^{18}$ neutrons/cm$^2$ to $1\times10^{19}$ neutrons/cm$^2$, or from $1\times10^{19}$ neutrons/cm$^2$ to $1\times10^{20}$ neutrons/cm$^2$. Useful neutron fluxes may range from $1\times10^{10}$ neutrons/cm$^2$/s to $1\times10^{19}$ neutrons/cm$^2$/s or more, such as from $1\times10^{11}$ neutrons/cm$^2$/s to $1\times10^{12}$ neutrons/cm$^2$/s, from $1\times10^{12}$ neutrons/cm$^2$/s to $1\times10^{13}$ neutrons/cm$^2$/s, from $1\times10^{13}$ neutrons/cm$^2$/s to $1\times10^{14}$ neutrons/cm$^2$/s, from $1\times10^{14}$ neutrons/cm$^2$/s to $1\times10^{15}$ neutrons/cm$^2$/s, from $1\times10^{15}$ neutrons/cm$^2$/s to $1\times10^{16}$ neutrons/cm$^2$/s, from $1\times10^{16}$ neutrons/cm$^2$/s to $1\times10^{17}$ neutrons/cm$^2$/s, from $1\times10^{17}$ neutrons/cm$^2$/s to $1\times10^{18}$ neutrons/cm$^2$/s, or from $1\times10^{18}$ neutrons/cm$^2$/s to $1\times10^{19}$ neutrons/cm$^2$/s.

The target aqueous suspension 205 can include water and dissolved target nuclide material in the liquid phase 215. As noted above, the target nuclide material 105 in FIG. 1 or 205 in FIG. 2 can be in the form of atomic or molecular ions. The target nuclide material may be one or more target nuclides. The target nuclide material may be in the form of a salt that is dissolved in the water, and thus the liquid phase (e.g., liquid phase 215) may contain counterions. The target nuclide salt(s) can be any salt of any element having an atomic number from 21 to 83 that dissolves in water. Advantageously, the target nuclide salt can be any salt of elements of the lanthanide series that dissolves in water, or any salt of elements of the platinum group metals (PGMs, such as rhodium, ruthenium, iridium and osmium) that dissolves in water, or any salt of rare earth elements that dissolves in water, or any salt of transition metals (e.g., first row, second row or third row transition metals) that dissolves in water, e.g., any salt that dissolves in water of any of the following elements: Yb, Lu, Re, Gd, Tb, Mo, Tc, Ho, Dy, Ir, Sn, Y, Pd, or Cr. Exemplary counterions may include cations, such as ammonium ions, sodium ions, potassium ions, or acid cations (e.g., organic acid counterions), in the case of the target nuclide material being an oxyanion or other molecular anion. Exemplary counterions may include anions, such as hydroxide, acetate, nitrate ions, phosphate ions, sulfate ions, halogen anions, in the case of the target nuclide material being a cation. Example target nuclide salts include, but are not limited to ytterbium (II) iodide, ytterbium (III) sulfate, ytterbium (III) oxide, ytterbium (III) acetate, ytterbium (III) phosphate, ytterbium (II) chloride, or ytterbium (II) nitrate, rhenium perrhenates such as sodium or ammonium perrhenates, lutetium sulfate, lutetium chloride, lutetium nitrate, lutetium acetate, gadolinium (III) nitrate, terbium (III) chloride hexahydrate, terbium (III) nitrate hexahydrate, molybdates such as ammonium molybdate, sodium molybdate, molybdic acid disodium salt, molybdic acid hexammonium salt, molybdenum zinc oxide, salts of the pertechnetate ion or oxoanion such as lithium pertechnetate, lithium pertechnetate monohydrate, pertechnetate trihydrate, sodium pertechnetate, sodium pertechnetate monohydrate, sodium pertechnetate dihydrate, sodium pertechnetate tetrahydrate, potassium pertechnetate, ammonium pertechnetate, rubidium pertechnetate, alpha or beta cesium pertechnetate, thalium pertechnetate, silver pertechnetate, holmium sulfate, holmium (III) acetate monohydrate, holmium chloride, holmium bromide, holmium iodide, holmium nitrate, dysprosium (III) chloride or dysprosium trichloride, dysprosium sulfate, hydrated iridium (III) chloride ($IrCl_3 \cdot (H_2O)_n$), Dihydrogen hexachloroiridate(IV) hydrate ($H_2[IrCl_6] \cdot 6\,H_2O$), tin divalent or tetravalent cation salts such as halide salts of tin divalent or tetravalent cation such as tin (II) chloride or stannous chloride or stannous chloride dihydrate, yttrium (III) chloride, yttrium bromide, yttrium iodide, yttrium nitrate, yttrium sulfate, palladium (II) chloride, palladium chloride dihydrate, palladium (II) sulfate, palladium (II) nitrate, palladium (II) acetate, salts (e.g., sodium, potassium, ammonium) of the form $M_2Pd$(Halogen, e.g., Cl, Br)$_{4\,or\,6}$, e.g., dipotassium tetrachloropalladate, dipotassium tetrabromopalladate, disodium tetrachloropalladate, disodium tetrabromopalladate, diammonium tetrachloropalladate, dipotassium hexachloropalladate, dipotassium hexabromopalladate, diammonium hexachloropalladate, chromium (III) oxide, chromium (III) hydroxide, chromic (III) acetate, chromium (III) nitrate, chromium (III) sulfate, chromium (III) chloride hexahydrate, chromium (VI) compounds such sodium chromate, and potassium chromate, amongst others. In some cases, it may be desirable to limit certain atomic species from the counterions, such as atomic species that may be activated upon exposure to neutrons and produce nuclides that can adsorb to the solid carbon nanostructured material similar to the process used for preparing the radioisotopes of interest herein. For example, in some cases, it may be desirable to use counterions that do not include sodium, sulfur, or chlorine atoms.

In some examples, the concentration of target nuclide material may range from 0.001 mg/ml to 1 mg/ml in the target aqueous suspension 205. For example, the concentration of the target nuclide material may be from 0.001 mg/ml to 0.005 mg/ml, from 0.005 mg/ml to 0.01 mg/ml, from 0.01 mg/ml to 0.05 mg/ml, from 0.05 mg/ml to 0.1 mg/ml, from 0.01 mg/ml to 0.5 mg/ml, or from 0.5 mg/ml to 1 mg/ml.

Figure 3:
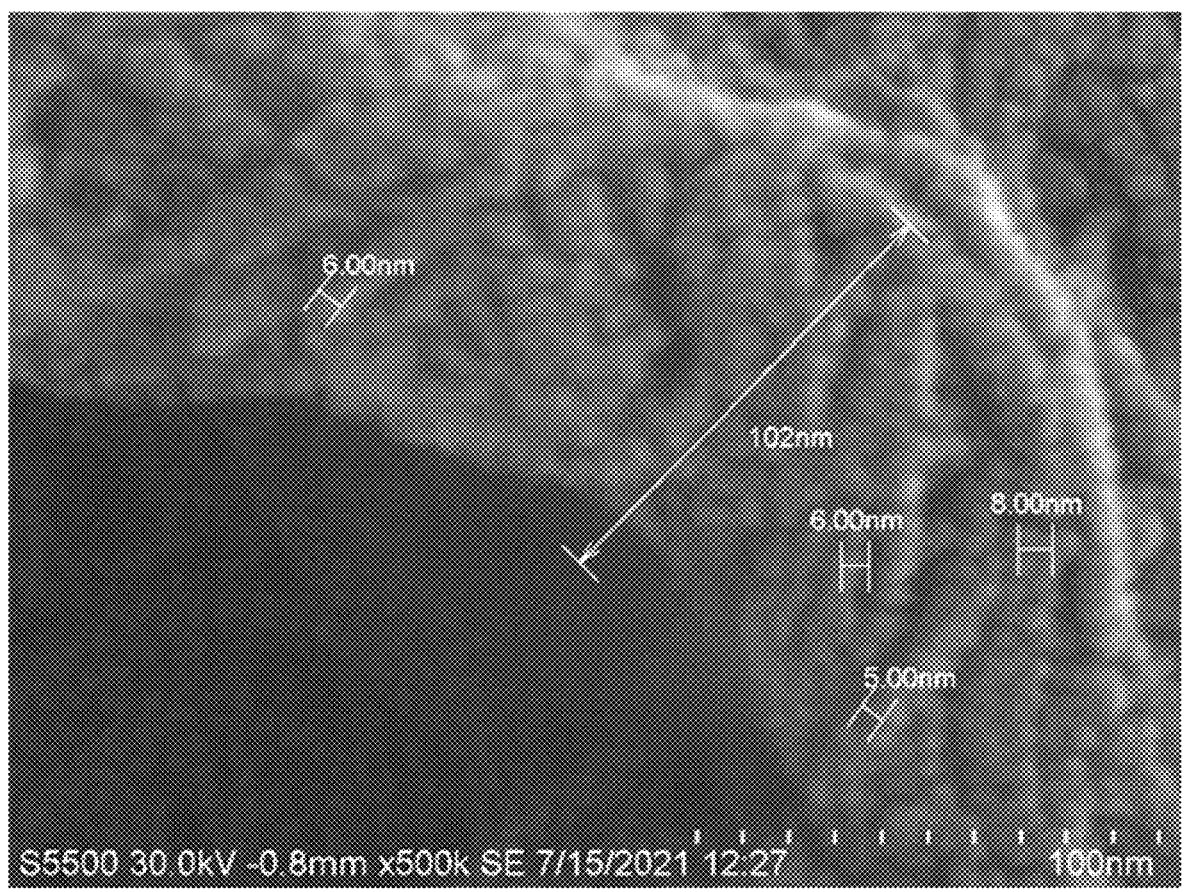
FIG. 3 provides a scanning electron microscope image of single walled carbon nanotubes (one example of solid carbon nanostructured material) in water demonstrating the carbon nanotubes' common behavior of inter-tube bonding.
Figure 4:
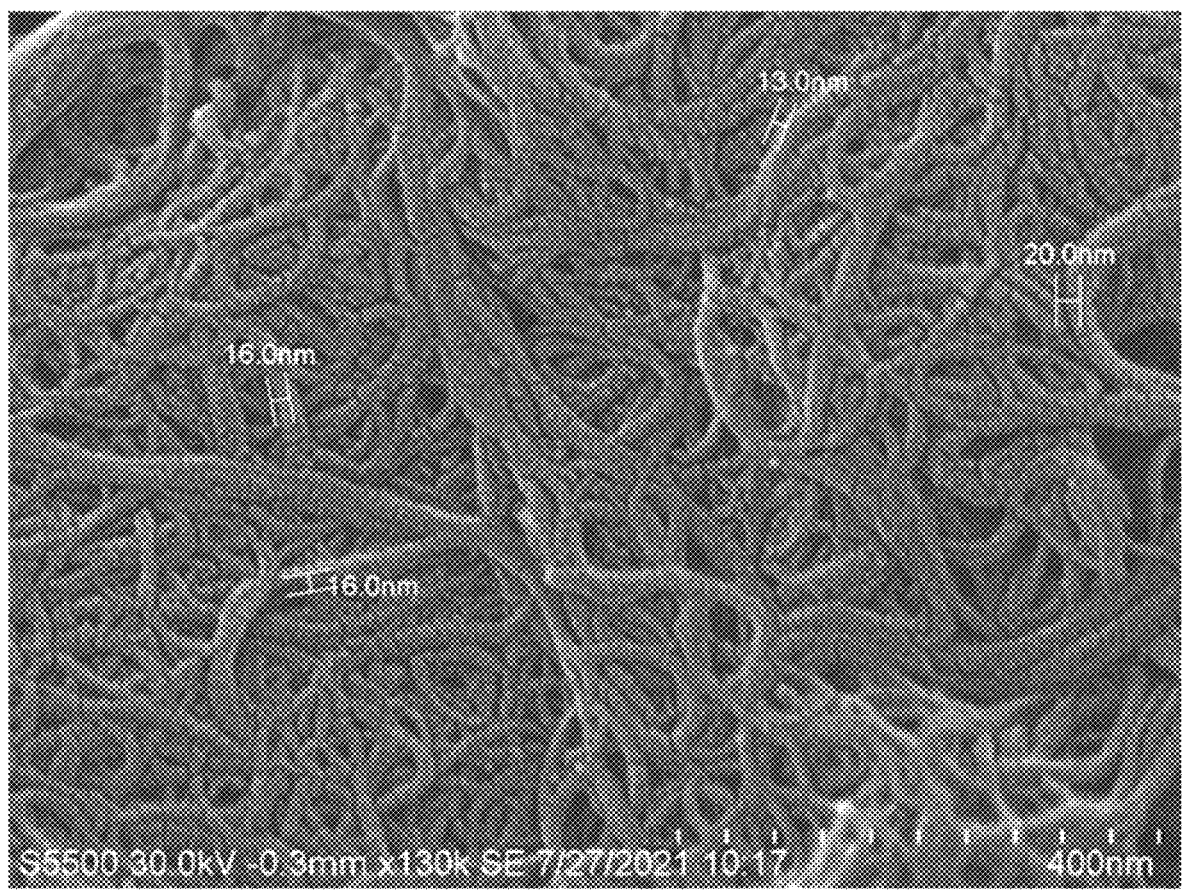
FIG. 4 provides a scanning electron microscope image of single walled carbon nanotubes in water following sonication. This demonstrates how the carbon nanotubes can be separated to remove inter-tube bonding but with limited spacing between tubes.
Figure 5:
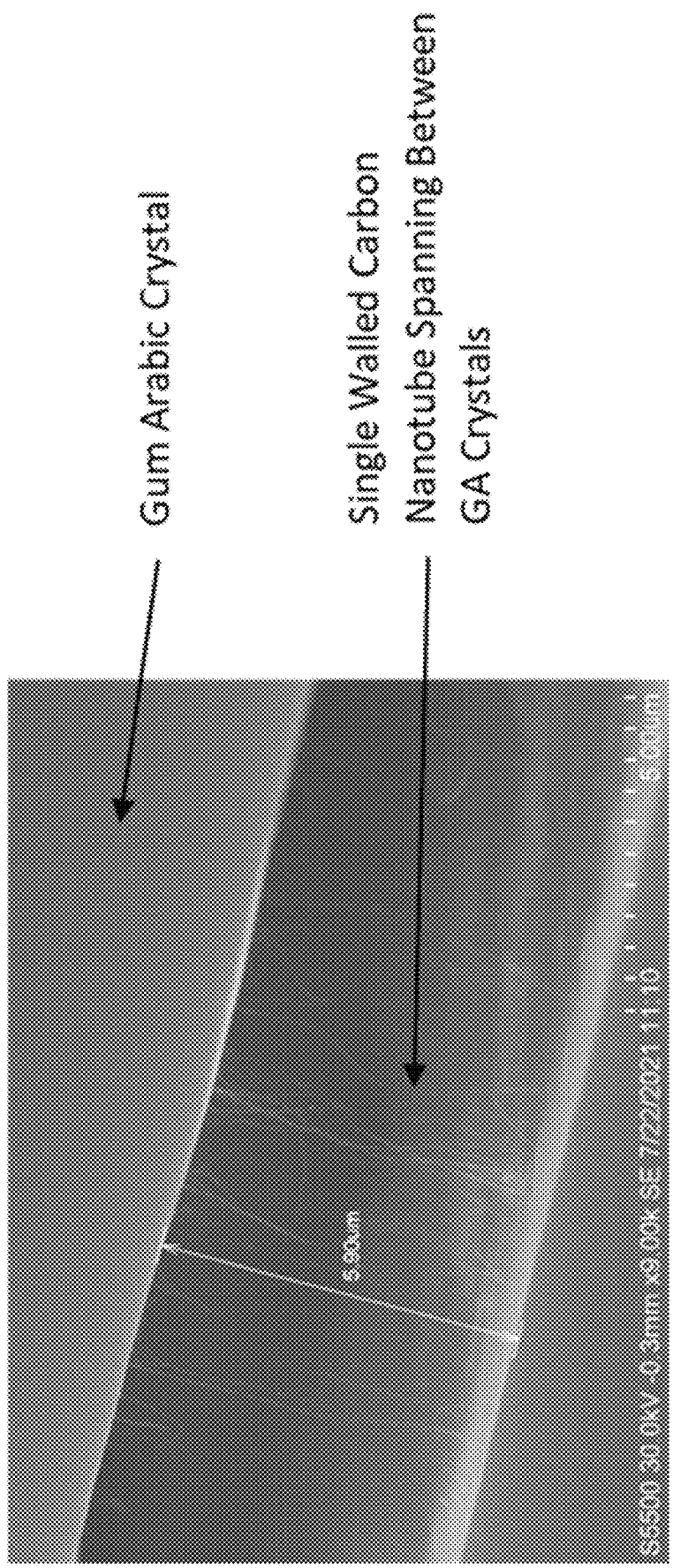
FIG. 5 provides a scanning electron microscope image of 1 ml solution of single walled carbon nanotubes in water with 15 weight percent gum arabic following sonication for 90 minutes and vortex mixing for 20 minutes. This demonstrates the separation and ordering of the carbon nanotubes spanning between the gum arabic crystals.

The target aqueous suspension 205 can further include a surfactant (e.g., a surface active agent), which can aid in dispersing the solid carbon nanostructured material 225 in the target aqueous suspension 205. The presence of the surfactant can be useful for preventing or reducing clumping or agglomeration of the solid carbon nanostructured material 225 and in ensuring uniform dispersion of the solid carbon nanostructured material 225 throughout the sample. FIG. 3 shows a scanning electron microscope image of carbon nanotubes in water demonstrating one form of clumping in which the tubes tend to bundle together via inter-tube bonding. FIG. 4 shows the separation of these tubes via sonication to remove much of the clumping. FIG. 5 shows the impact of the addition of a surfactant such as gum arabic (followed by sonication and vortex mixing) to the aqueous suspension. In this case, the carbon nanotubes are fully separated and spanning between the gum arabic crystals. This separation allows for the target material to be spaced between individual nanotubes. In some examples, a concentration of the solid carbon nanostructured material 225 in the target aqueous suspension 205 may be from 0.001 mg/ml to 10 mg/ml, such as from 0.001 mg/ml to 0.005 mg/ml, from 0.005 mg/ml to 0.01 mg/ml, from 0.01 mg/ml to 0.05 mg/ml, from 0.05 mg/ml to 0.1 mg/ml, from 0.1 mg/ml to 0.5 mg/ml, from 0.5 mg/ml to 1 mg/ml, from 1 mg/ml to 5 mg/ml or from 5 mg/ml to 10 mg/ml. In some examples, an amount of the solid carbon nanostructured material 225 in the target aqueous suspension 205 may have a mass ratio to the target nuclide material of from 1:1 to 100:1, such as from 1:1 to 5:1, from 5:1 to 10:1, from 10:1 to 50:1, or from 50:1 to 100:1.

Figure 6:
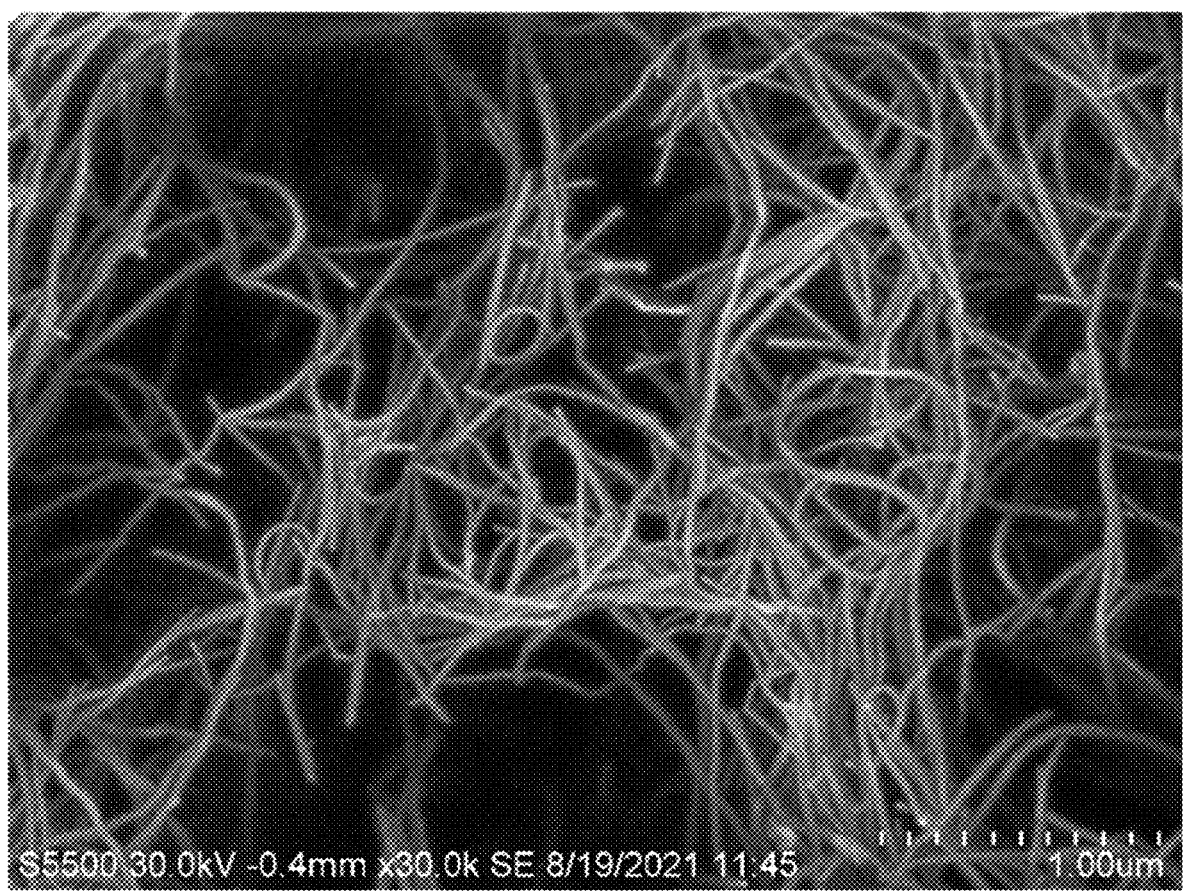
FIG. 6 provides a scanning electron microscope image of 1 ml solution of single walled carbon nanotubes at 3 mg/ml in water with 8 weight percent Triton X-100 following sonication for 90 minutes and vortex mixing for 20 minutes. This demonstrates the separation of the carbon nanotubes via the surfactant but with less ordering as is found with gum arabic.

Exemplary surfactants are anionic surfactants, amphoteric surfactants, nonionic surfactants, cationic surfactants, or polysaccharide surfactants. Exemplary anionic surfactants include, but are not limited to, water-soluble soaps and water-soluble synthetic surface-active compounds, such as soaps that are the alkali metal, alkaline earth metal, and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts; and such as synthetic surfactants, for instance, fatty sulfonates, fatty sulfates, sulfonated benzimidazole derivatives, or alkylarylsulfonates, with the fatty sulfonates and sulfates typically in the form of alkali metal, alkaline earth metal, or substituted or unsubstituted-ammonium salts, and in general have an alkyl radical of 8 to 22 C atoms, with alkyl also including the alkyl moiety of acyl radicals; e.g., the sodium or calcium salt of ligninsulfonic acid, of dodecylsulfuric acid ester or of a fatty alcohol sulfate mixture prepared from naturally occurring fatty acids. Anionic surfactants also include, but are not limited to, the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids (e.g., phosphatidylcholine (lecithin)), can further also be used. Further exemplary anionic surfactants include, but are not limited to, sulfate surfactants, sulfonate surfactants, phosphate surfactants, or carboxylate surfactants. Amphoteric surfactants are surfactants simultaneously carrying the anionic and cationic hydrophilic group with its structure containing simultaneously hermaphroditic ions which are able to form cation or anion according to the ambient conditions (such as pH changes). Amphoteric surfactants can thus have two types of groups, one of which is pH sensitive while the other is not sensitive at all pH ranges. From the practical perspective, the usually adopted cationic part is an amine salt or quaternary ammonium hydrophilic group while the anionic moiety is a carboxylate, sulfonate, phosphate hydrophilic group, especially the amino acid type amphoteric surfactants that contains both amino and carboxy group or the intramolecular ammonium salt type amphoteric surfactants consisting of carboxyl group and a quaternary ammonium group. Exemplary amphoteric surfactants include, but are not limited to, betaine surfactants or substituted lauryl compounds of betaine, amino oxide surfactants, primary amine surfactants, secondary amine surfactants, tertiary amine surfactants, or quaternary ammonium surfactants, e.g., lauryl betaine, betaine citrate, sodium lauroamphoacetate, sodium hydroxymethylglycinate, cocoamidopropyl betaine. Exemplary nonionic surfactants include, but are not limited to, polyglycol ether derivatives of aliphatic or cycloaliphatic alcohols, saturated or unsaturated fatty acids, and alkylphenols, which can contain 3 to 30 glycol ether groups and 8 to 20 carbon atoms in the (aliphatic) hydrocarbon radical and 6 to 18 carbon atoms in the alkyl radical of the alkylphenols; water-soluble polyethylene oxide adducts, containing 20 to 250 ethylene glycol ether groups and 10 to 100 propylene glycol ether groups, or propylene glycol, ethylene diaminopolypropylene glycol, and/or alkyl polypropylene glycol with there being 1 to 10 carbon atoms in the alkyl chain, and such compounds usually containing 1 to 5 ethylene glycol units per propylene glycol unit; ethoxylate surfactants, fatty alcohol ethoxylate surfactants, alkoxylate surfactants, alkyl polyglycoside surfactants, or cocamide surfactants—for instance, surfactants available from DOW under the name TRITON, such as TRITON X-100, TRITON X-45, TRITON X-200, TRITON X-15, amongst others. FIG. 6 shows the impact of the addition of TRITON X-100 as a surfactant (followed by sonication and vortex mixing) to an aqueous suspension of SWCNT. The carbon nanotubes are fully separated compared to that shown in FIG. 4, leaving space between the individual nanotubes for the target material. Additional example surfactants include nonylphenol-polyethoxyethanols, castor oil polyglycol ethers, polypropylene-polyethylene oxide adducts, tributylphenoxypoly-ethoxyethanol, polyethylene glycol and octylphenoxypolyethoxyethanol, as well as fatty acid esters of polyoxyethylene sorbitan, such as polyoxyethylene sorbitan trioleate. Polyethylene glycol surfactants are also known as CARBOWAX and CARBOWAX SENTRY. Polyoxyethylene sorbitan ester surfactants are also commonly referred to as Tweens, sorbitan esters are sometimes referred to as SPANs, and exemplary polyoxyethylene sorbitan ester surfactants include Tween 80, polysorbate 20 and polysorbate 80. Polyoxyethylene fatty ethers derived from lauryl, cetyl, stearyl and oleyl alcohols (known as Brij surfactants), such as triethyleneglycol monolauryl ether (Brij 30) and polyoxyethylene-9-lauryl ether surfactants are also useful in the practice of the invention. Surfactants also useful in the practice of the invention include copolymers of ethylene oxide (EO), propylene oxide (PO), and/or butylene oxide (BO), or Poly(ethylene oxide) surfactants. Exemplary cationic surfactants include, but are not limited to, quaternary ammonium salts which contain, as substituents, at least one alkyl radical having 8 to 22 C atoms and, as further substituents, lower, non-halogenated, or halogenated alkyl, benzyl, or lower hydroxyalkyl radicals, wherein the salts are preferably in the form of halides, methyl-sulfates, or ethyl-sulfates, with examples including stearyltrimethyl-ammonium chloride and benzyl-di-(2-chloroethyl)-ethyl-ammonium bromide; and alkyl ammonium chloride surfactants. Exemplary polysaccharide surfactants include, but are not limited to, gum arabic, bovine serum albumin, gelatin, chitosan, polysaccharides; and an example of a protein-based surfactant includes collagen proteins such as hydrophilic, collagen-containing calcium-dependent lectins also known as collectins. Other examples surfactants that can be used include gum arabic (GA), sodium dodecyl sulfate (SDS), sodium dodecyl benzene sulfonate (SDBS), cetyltrimethylammonium bromide (CTAB), polyvinyl pyrrolidone (PVP) and Tween 20. Advantageously, the surfactant can be biodegradable or metabolizable and biocompatible; also advantageously, surfactants can have antibacterial properties. Optionally, graphene oxide may be used as a surfactant. In some embodiments, the surfactant can be a mixture of surfactants. In some cases, it may be desirable to limit certain atomic species from the surfactants, such as atomic species that may be activated upon exposure to neutrons and produce nuclides that can adsorb to the solid carbon nanostructured material similar to the process used for preparing the radioisotopes of interest herein. For example, in some cases, it may be desirable to use surfactants that do not include sodium, sulfur, or chlorine atoms.

In some examples, the concentration of the surfactant in the target aqueous suspension 205 may be from 0.001 mg/ml to 300 mg/ml, such as from 0.001 mg/ml to 0.003 mg/ml, from 0.003 mg/ml to 0.01 mg/ml, from 0.01 mg/ml to 0.03 mg/ml, from 0.03 mg/ml to 0.1 mg/ml, from 0.1 mg/ml to 0.3 mg/ml, from 0.3 mg/ml to 1 mg/ml, from 1 mg/ml to 3 mg/ml, from 3 mg/ml to 10 mg/ml, from 10 mg/ml to 30 mg/ml, from 30 mg/ml to 100 mg/ml, or from 100 mg/ml to 300 mg/ml.

Figure 7:
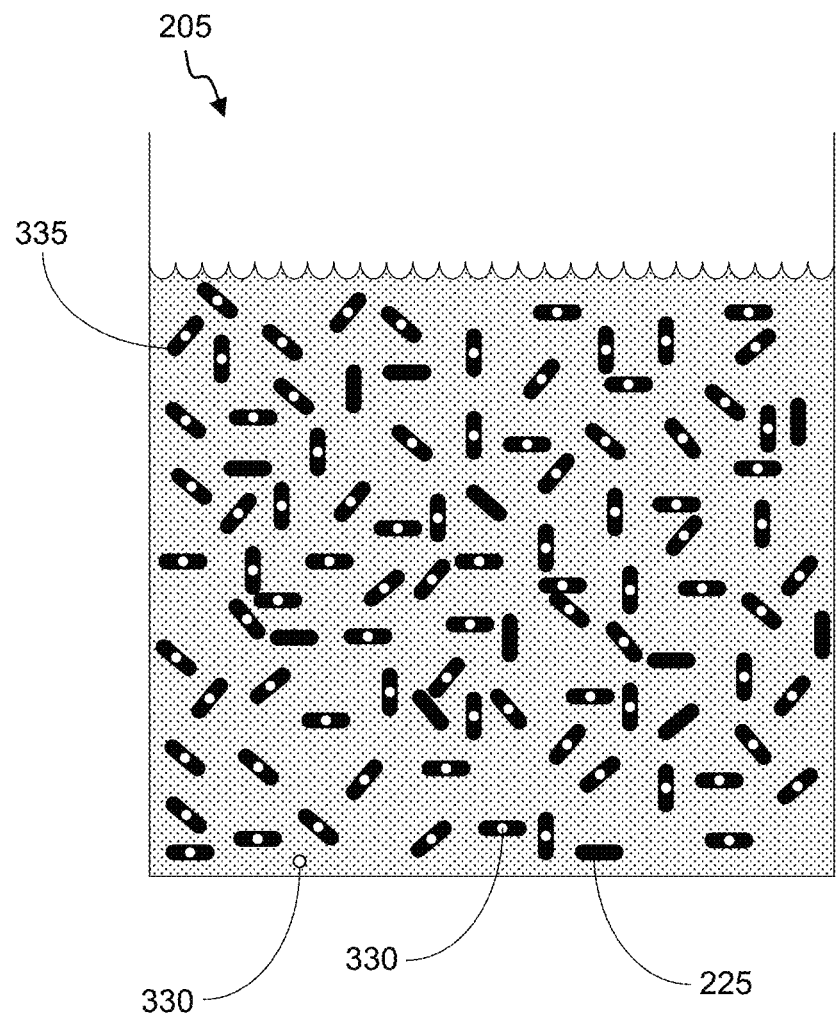
FIG. 7 provides a schematic illustration of a target solution with suspended solid carbon nanostructured material after neutron irradiation, showing radionuclides adsorbed to the solid carbon nanostructured material.

Turning next to FIG. 7, upon exposure of the target nuclide material in the target aqueous suspension 205 to neutrons 210, some of the target nuclide material can capture neutrons and generate radionuclides 330 that recoil and are adsorbed to the solid carbon nanostructured material 225. An amount of the radionuclides 330 may remain in the solution of the target aqueous suspension 205. The solid carbon nanostructured material 225 having adsorbed radionuclides 330 may be referred to herein as loaded solid carbon nanostructured material 335.

Figure 8:
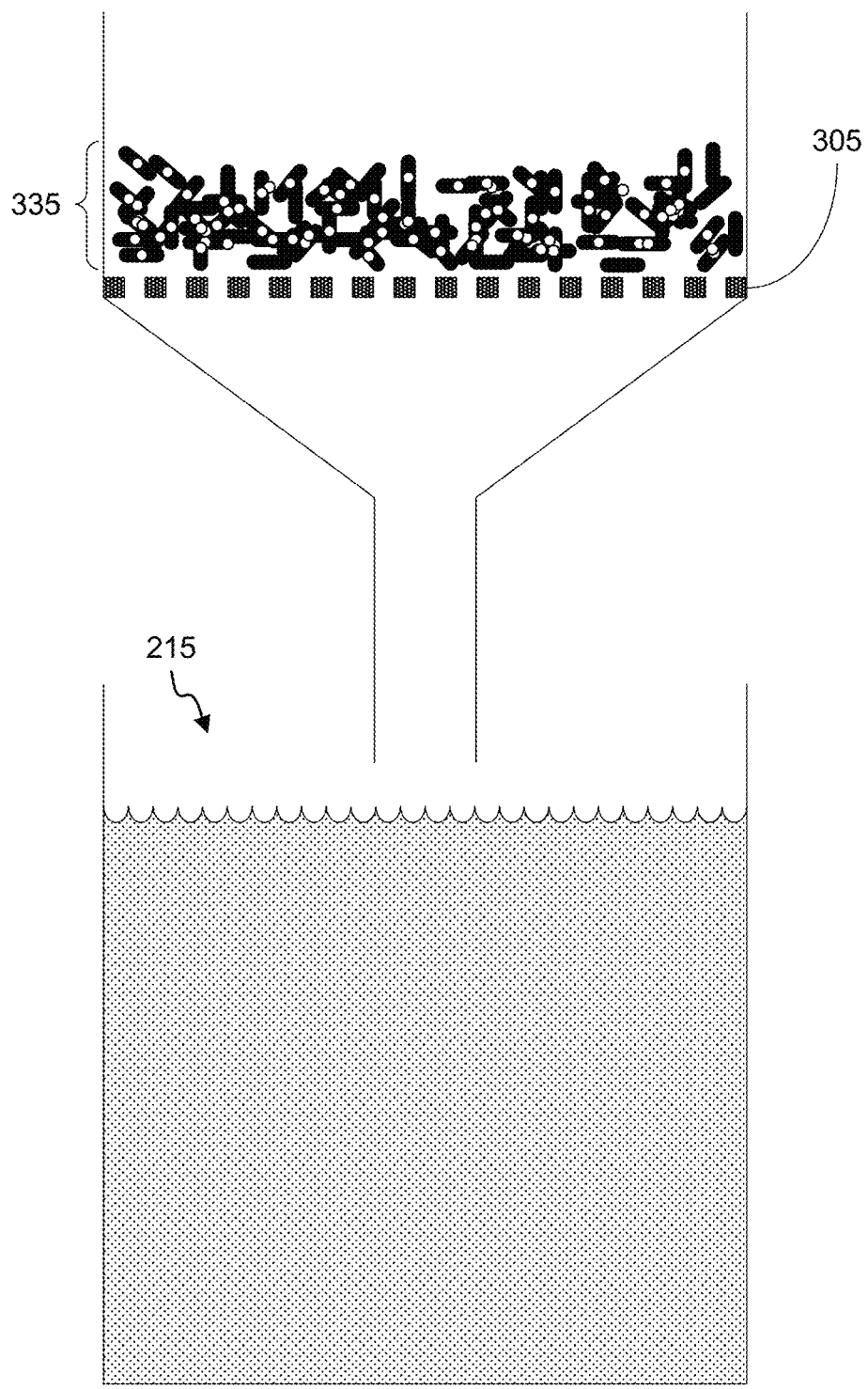
FIG. 8 provides a schematic illustration of separation of solid carbon nanostructured material with adsorbed radionuclides from a target solution.
Figure 9:
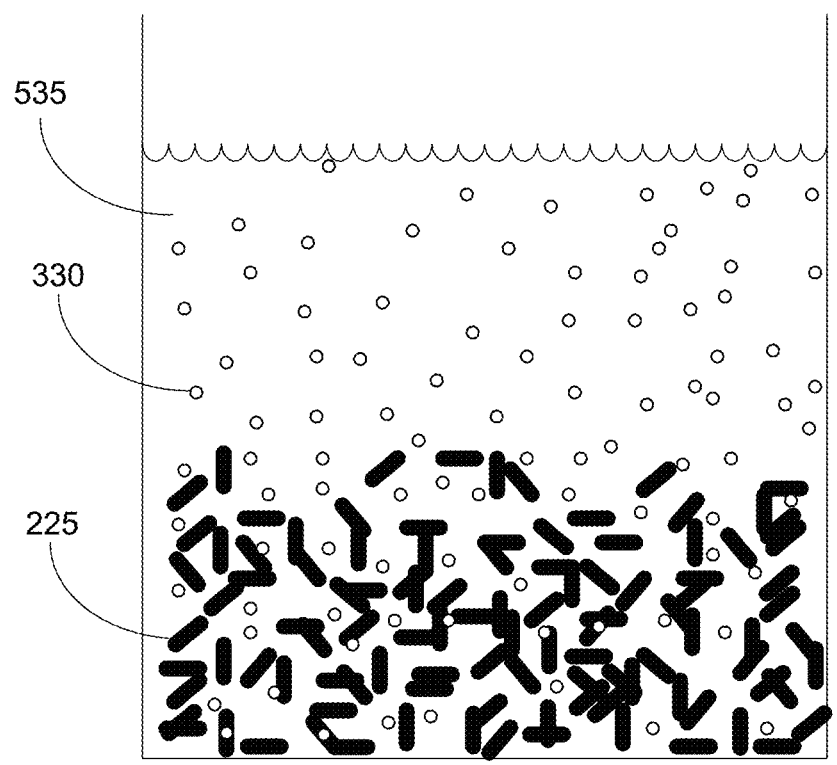
FIG. 9 provides a schematic illustration of separation of adsorbed radionuclides from a solid carbon nanostructured material, such as by treatment with an acidic solution.

In order to separate the radionuclides 330 from the target nuclides in the liquid phase 215 of the target aqueous suspension 205, the target aqueous suspension 205 with loaded solid carbon nanostructured material 335 may be subjected to a separation process. FIG. 8 shows an exemplary filtration process, but other separation techniques may be used. FIG. 8 shows a filter medium 305 used to collect the loaded solid carbon nanostructured material 335 while allowing the liquid phase 215 to pass through for separate collection. Liquid phase 215 may contain the remaining target nuclide material and may advantageously be recycled, where additional solid carbon nanostructured material can be dispersed therein, for subsequent exposure to a neutron source for generation of additional radionuclides. Filtered loaded solid carbon nanostructured material 335 can be optionally washed and collected for subsequent use or treatment.

As shown in FIG. 8, the loaded solid carbon nanostructured material can be processed to release the radionuclides 330 from the solid carbon nanostructured material 225. Here, the loaded solid carbon nanostructured material is washed with an acidic solution 535, such as a solution containing a mineral acid, an organic acid, or a complexant. Wash solutions used to release the radionuclides may also be referred to herein as release solutions. Exemplary wash solutions include, but are not limited to, hydrochloric acid solutions, nitric acid solutions, sulfuric acid solutions, ascorbic acid solutions, acetic acid solutions, oxalic acid solutions, citric acid solutions, or polyaminocarboxylates solutions, such as ethylenediaminetetraacetic acid (EDTA), tetraxetan (DOTA), or dodecane tetraacetic acid (DTPA). Stirring, sonication, or other mechanical agitation may be used to facilitate release of the radionuclides 330 from the solid carbon nanostructured material 225. Wash solutions may use concentrations from 0.01 M to 5.0 M, such as from 0.01 M to 0.1 M, from 0.1 M, to 1 M, from 1 M to 2 M, from 2 M to 3 M, from 3 M to 4 M, or from 4 M to 5 M. In specific examples, a wash solution may comprise 0.1 M hydrochloric acid, 1.0 M hydrochloric acid, 1.0 M nitric acid, 0.1 M DOTA at pH=2, or 0.1 M DOTA at pH=7.5.

The liquid solution containing radionuclides 330 can optionally be subjected to further processing or used as is. In some cases, washing can be followed by a further separation to separate the radionuclides 330 in solution from the solid carbon nanostructured material 225. In some cases, the washing process can take place following the filtration process, such as shown in FIG. 8, using the same filter medium, but collecting the wash solution in a separate vessel and optionally recycling the wash solution through the filter medium and solid carbon nanostructured material 225 multiple times. The wash solution separated from the solid carbon nanostructured material 225 may be or represent a concentrated form of the radionuclides 330. For example, a ratio of the radionuclides 330 to stable or longer-lived nuclides of the same atom may be from 0.1:1 to 800:1, such as from 0.1:1 to 0.5:1, from 0.5:1 to 1:1, from 1:1 to 5:1, from 5:1 to 10:1, from 10:1 to 50:1, from 50:1 to 100:1, from 100:1 to 200:1, from 200:1 to 300:1, from 300:1 to 400:1, from 400:1 to 500:1, from 500:1 to 600:1, from 600:1 to 700:1, or from 700:1 to 800:1. Optionally, the solution of the radionuclides 330 may have a specific activity of from 50 GBq/mg to 9000 GBq/mg, such as from 50 GBq/mg to 9000 GBq/mg, such as from 50 GBq/mg to 100 GBq/mg, from 100 GBq/mg to 500 GBq/mg, from 500 GBq/mg to 1000 GBq/mg, from 1000 GBq/mg to 2000 GBq/mg, from 2000 GBq/mg to 3000 GBq/mg, from 3000 GBq/mg to 4000 GBq/mg, from 4000 GBq/mg to 5000 GBq/mg, from 5000 GBq/mg to 6000 GBq/mg, from 6000 GBq/mg to 7000 GBq/mg, from 7000 GBq/mg to 8000 GBq/mg, or from 8000 GBq/mg to 9000 GBq/mg.

The invention may be further understood by the following non-limiting examples.

EXAMPLE 1

Production of Lu-177 Using Ytterbium Nitrate Solution with SWCNT Suspended with Gum Arabic Lu-177 is a radioactive isotope (half-life of 6.7 days) in high demand as a therapeutic for the treatment of several types of cancer and may have other nuclear medicine applications. Current estimates are that the demand for Lu-177 will exceed 190,000 doses per year by 2023. To generate a no-carrier-added sample of Lu-177, it can be produced by irradiation (typically between 5-10 days) of enriched Yb-176 in a nuclear reactor. The Yb-176 absorbs a neutron and produces Yb-177 (half-life of 1.9 hours), which decays quickly to Lu-177. This is also referred to as the "Indirect" route for the production of Lu-177 (as opposed to the "Direct" route of irradiation of enriched Lu-176). After a short decay following irradiation (approximately 18-24 hours), the Lu-177 can be chemically separated from the Yb to produce the product Lu-177 material. The Yb can then be recovered so that it can be re-irradiated to produce additional Lu-177. The chemical separation of the Lu-177 from the unirradiated Yb is a challenging task as all members of the lanthanide series tend to act in a chemically similar manner, especially since the concentration of Lu-177 in the material is extremely small. The methods described below and herein can allow for a faster, more efficient, and less waste intensive means of separation to produce Lu-177 than by the traditional method just described above in this example.

Preliminary studies were conducted to determine the efficacy of the Szilard-Chalmers reaction in a variety of experimental configurations. A successful configuration would result in a high percentage of the radioactivated product being captured by a solid adsorber, a short time required for separation with limited waste production, a high recovery of the unirradiated enriched target material during separation from the solid adsorber, and/or a high percentage of recovery of the radioactivated product back out of the solid adsorber. These factors are important for a useful, cost-effective, and efficient process. This Example describes a production method using a liquid target and solid adsorber for high specific activity radioactive products.

Seven samples were prepared using 6-20 mg of SWCNT added to 2 ml of a solution of gum arabic in water (with 15% gum arabic by mass). A quantity of ytterbium nitrate in an aqueous solution was added to each sample to result in seven samples with varying mass ratios of SWCNT to Yb. The quantity of ytterbium nitrate solution (standard solution of 12.355 mg Yb/mL) and SWCNT added to produce samples with SWCNT to Yb mass ratios of 1:1, 5:1, 10:1, 15:1, 20:1, 25:1, and 30:1 is given in Table 1. Each sample was vortex mixed for 1 minute and then sonicated at an initial temperature of 25 degrees Celsius for 4 hours. The addition of a surfactant to the reaction mixture effectively suspended the carbon adsorber in solution.

TABLE 1

SWCNT Mass and Yb Solution Volumes Used in Sample Preparations.

| Ratio (SWCNT:Re) | Mass of SWCNT (mg) | Volume of Yb Solution (μL) |
| --- | --- | --- |
| 1:1 | 6.85 | 554 |
| 5:1 | 6.58 | 107 |
| 10:1 | 10.00 | 81 |
| 15:1 | 19.82 | 108 |
| 20:1 | 19.81 | 80 |
| 25:1 | 19.71 | 64 |
| 30:1 | 19.88 | 54 |

The samples were irradiated in a nuclear reactor for 30 min at a total neutron flux of $5 \times 10^{12}$ n/cm$^2$/sec. The samples were allowed to decay for a short period of time prior to handling. The liquid target material was then separated from the solid SWCNTs via centrifugation (within 4 hours of irradiation) at 5500 rpm for 5 minutes, and the liquid target material was collected. The remaining SWCNT were washed three times with 2 ml of water to remove any residual unirradiated material. The activity of the unirradiated target material and the SWCNT were individually measured using high-resolution gamma spectroscopy. Table 2 shows the percent of radioactivity captured on the carbon nanostructured adsorber as a function of the SWCNT to Yb mass ratio. Increasing the quantity of SWCNT in the sample resulted in substantially more uptake of the radioactive isotopes on the carbon adsorber. The addition of the surfactant increased uptake from 10 to 84%. Note: other than during sonication all steps in the experiment were performed at room temperature and all water used was deionized water (pH=6.19).

TABLE 2

Percent of Activity Captured on Solid SWCNT Adsorber as a Function of SWCNT to Yb Mass Ratio.

| Mass Ratio of SWCNT to Yb | Percent of Activity Captured by SWCNT |
| --- | --- |
| 1:1 | 10.4% |
| 5:1 | 23.2% |
| 10:1 | 49.5% |
| 15:1 | 70.8% |
| 20:1 | 76.5% |
| 25:1 | 78.2% |
| 30:1 | 84.2% |

Following the separation, a series of experiments were performed to determine the quantitative recovery of the activated products from the SWCNTs. Acidic solutions, HCl (0.1 and 1.0 M), HNO$_3$ (1.0 M), and DOTA (0.1 M at both 2 and 7.5 pH values) were investigated as potential stripping agents. A 2 mL volume of each stripping agent was added to an approximate 5 mg aliquot of the SWCNT from the experiment described above. Each SWCNT and stripping agent mixture was vortex mixed for an hour and centrifuged at 5500 rpm for 5 minutes for separation at standard temperature and pressure. Two identical successive extractions were performed for each mixture. Table 3 lists the results for the removal of the activated nuclides from the solid adsorber. Following final centrifugation of the SWCNT from the unirradiated target solution, 98.9% of the radioactivity was released from the SWCNTs in two identical sequential extractions of 1.0 M HCl using the same procedure as described above. Similar results were obtained for the 1.0 M HNO$_3$ stripping agent using the same procedure as described above, where 97.8% of the activated products were removed from the SWCNTs. The removal of the radioactive nuclides exhibited a decrease when either 0.1 M HCl or DOTA were used using the same procedure as described above.

TABLE 3

Percent of Activity Recovered from SWCNT with Stripping Agents HCl, HNO$_3$, and DOTA.

| Stripping Agent | Percent of Activity Removed from SWCNT |
| --- | --- |
| 0.1M HCl | 84.2% |
| 1.0M HCl | 98.9% |
| 1.0M HNO3 | 97.8% |
| 0.1M DOTA (pH = 2) | 56.2% |
| 0.1M DOTA (pH = 7.5) | 70.0% |

This example demonstrates a procedure using an aqueous solution of ytterbium nitrate with SWCNTs suspended with a gum arabic surfactant that results in over 84% of the radioactive product (Lu-177) being collected by the carbon adsorber when the SWCNT to Yb mass ratio is 30:1. Recovery of over 98% of the radioactive product (Lu-177) from the SWCNT was shown to be accomplished using two identical, successive extractions with 1.0 M HCl. This results in a high specific activity Lu-177 sample in the form of lutetium chloride in an aqueous solution that would be suitable as a raw material for manufacturing several radiopharmaceuticals.

COMPARATIVE EXAMPLE 2

Production of Lu-177 Using Ytterbium Oxalate Solid with DOTA Solution Capture Material Experiments were performed to explore the possibility of using a solid target material with a liquid capture material as a comparative to Example 1. This demonstrates a method that is not productive. In this Example, solid ytterbium oxalate, a target material that is insoluble in aqueous media, was prepared by vortex mixing in an aqueous solution of DOTA. Solutions of 1, 2, and 4 moles of DOTA to Yb were prepared each with a volume of 0.5 mL. Prior to irradiation, each solution was centrifuged for 10 minutes at 5500 rpm, and the aqueous phase was pipetted away from the solute; this aliquot was labeled as "wash 1". A fresh DOTA solution was then added, and this process was repeated to produce a "wash 2" aliquot. After two successive "washes", the ytterbium oxalate target material was again vortex mixed with the DOTA solution. The solution was then irradiated at a total neutron flux of $3 \times 10^{12}$ n/cm$^2$/sec for 30 minutes. After irradiation, the samples were allowed to decay overnight prior to handling. The samples were then centrifuged a final time for 10 minutes at 5500 rpm and the liquid DOTA removed from the solid ytterbium oxalate. The liquid DOTA and the solid ytterbium oxalate were then individually analyzed by high-resolution gamma spectroscopy to determine the activity of Lu-177 captured in the liquid DOTA capture material.

The percent of Lu-177 activity captured by the DOTA for each of the three samples is shown in Table 4. None of the cases resulted in a significant capture of the irradiated material. The solid target material aggregated near the bottom of the irradiation vial which restricted the number of contact sites between the target and the adsorber. This result may be considered unsuccessful due to the limited surface area of the solid ytterbium available to the DOTA solution. The recoil nuclides produced from the Szilard-Chalmers effect have a limited range, such that no solid target material will likely be successful as a means for radionuclide production using this capture technique.

TABLE 4

Percent of Activity Captured on DOTA (1, 2, and 4 moles of DOTA to 1 Yb) From a Solid Ytterbium Oxalate Target.

| Mole Ratio of DOTA to Yb | Percent of Activity Capture by DOTA |
|---|---|
| 1:1 | 5.24% |
| 2:1 | 5.57% |
| 4:1 | 5.60% |

EXAMPLE 3

Production of Re-186 Using Perrhenic Acid Solution Target and SWCNT Capture Material Suspended with Graphene Oxide Re-186 (half-life of 90 hours) is another reactor-produced radioisotope of medical interest. Re-186 is currently employed for bone pain palliation, intravascular radiotherapy, and as a radiolabeling agent for antibodies and peptides. Re-186 can be produced through neutron irradiation of enriched Re-185. This directly produced Re-186 is referred to as the "carrier added" form. Samples of Re-186 are typically at a low specific activity since they contain the unirradiated Re-185 in addition to the product isotope of Re-186. Some uses of Re-186, such as radiolabeling, require the use of high specific activity material. The methods provided in the instant disclosure allow for capture of the Re-186 on the solid adsorber, which will in turn allow for a physical separation of the product Re-186 from the unirradiated Re-185, leading to preparation of a relatively high specific activity Re-186 product.

In this Example, the production of Re-186 was conducted according to the techniques generally outlined in Example 1, but by preparation of a sample using Re-185 in the form of perrhenic acid (in a nitric acid solution) as the target material, instead of ytterbium nitrate as used in Example 1, with SWCNTs, as the capture material, suspended using Graphene Oxide (GO). 10 mg of SWCNT and 0.5 mg of Re in the form of perrhenic acid was added to a 5 ml solution of GO and water with a GO concentration of 1.0 mg/ml. The sample was vortex mixed for 1 minute and then sonicated at an initial temperature of 25 degrees Celsius for 4 hours. The GO, acting as a surfactant to the mixture, effectively suspended the carbon adsorber (SWCNTs) in solution, similar to the use of gum arabic as used in Example 1. The samples were irradiated in a nuclear reactor for 30 min at a total neutron flux of $5 \times 10^{12}$ n/cm$^2$/sec. The samples were allowed to decay for a short period of time prior to handling. The liquid target material was then separated from the solid SWCNTs via centrifugation (within 4 hours of irradiation) at 5500 rpm for 5 minutes, and the liquid target material was collected. The remaining SWCNT were washed three times with 2 ml of water to remove any residual unirradiated material. The activity of the unirradiated target material and the SWCNT were individually measured using high-resolution gamma spectroscopy. The measurement showed that 73.8% of the Re-186 activity was captured on the SWCNT, showing that the GO was successful at suspending and dispersing the capture material in the solution. Note: other than during sonication, all steps in the experiment were performed at room temperature and all water used was deionized water (pH=6.19).

EXAMPLE 4

Variations for Production of Lu-177

Techniques for production of Lu-177 are performed using the general principles outlined in Example 1, but using various different reagents and materials. An aqueous solution including Yb-176 atoms as a target nuclide in the form of a cation, as described above in Example 1, or a molecular anion is prepared, but any suitable soluble Yb-176 salts can be used in place of or in addition to ytterbium nitrate. In this Example, the Yb-176 salt is a Yb-176 sulfate salt, a Yb-176 phosphate salt, or a sodium, potassium, or ammonium ytterbate salt of Yb-176. The Yb-176 salt is added to the aqueous solution to achieve any desired concentration of Yb-176 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Yb-176 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Yb-177 and/or Lu-177 become adsorbed to the solid carbon nanostructured material. In some cases, adsorbed Yb-177 decays to generate adsorbed Lu-177.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Lu-177, as described above in Example 1. Release solutions are described above. The loaded carbon nanostructured and release solution is optionally subjected to stirring, sonication, or other mechanical agitation to facilitate release of the Lu-177 from the solid carbon nanostructured material into the release solution.

The release solution is subjected to a separation to separate the solid carbon nanostructured material from the liquid containing dissolved Lu-177 using a centrifugation process, as described above in Example 1. Other separation processes can be used, such as a filtration process. The process achieves a specific activity of Lu-177 of from 50 GBq/mg to 9000 GBq/mg or any specific activity or subrange within this range and/or a ratio of Lu-177 to Yb-176 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 5

Variations for Production of Re-186

Techniques for production of Re-186 are performed using the general principles outlined in Examples 1 and 3, but using various different reagents and materials. An aqueous solution including Re-185 atoms as a target nuclide in the form of a cation, as described above in Example 1, or a molecular anion, as described above in Example 3, is prepared, but any suitable soluble Re-185 salts can be used in place of ytterbium nitrate (Example 1) or in place of or in addition to perrhenic acid (Example 3). In this Example, the Re-185 salt is a Re-185 sulfate salt, a Re-185 phosphate salt, or a sodium, potassium, or ammonium perrhenate salt of Re-185. The Re-185 salt is added to the aqueous solution to achieve any desired concentration of Re-185 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Re-185 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1\times10^{13}$ neutrons/cm$^2$ to $1\times10^{20}$ neutrons/cm$^2$ or any fluence or subrange within this range. As a consequence of the irradiation process, atoms of Re-186 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Re-186, similar to the release of Lu-177 as described above in Example 1. Release solutions are described above. The loaded carbon nanostructured and release solution is optionally subjected to stirring, sonication, or other mechanical agitation to facilitate release of the Re-186 from the solid carbon nanostructured material into the release solution.

The release solution is subjected to a separation to separate the solid carbon nanostructured material from the liquid containing dissolved Re-186 using a centrifugation process, as described above in Example 1. Other separation processes can be used, such as a filtration process. The process achieves a specific activity of Re-186 of from 50 GBq/mg to 9000 GBq/mg or any specific activity or subrange within this range and/or a ratio of Re-186 to Re-185 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 6

Production of Gd-161

Techniques for production of Gd-161 are performed using the general principles outlined in Example 1, but using various different reagents and materials. An aqueous solution including target nuclide atoms in the form of a cation, as described above in Example 1, or a molecular anion, is prepared, but any suitable soluble Gd-160 salt is used in place of ytterbium nitrate. In this Example, the Gd-160 salt is a Gd-160 nitrate salt, a Gd-160 sulfate salt, a Gd-160 phosphate salt, or a sodium, potassium, or ammonium gadolinate salt of Gd-160. The Gd-160 salt is added to the aqueous solution to achieve any desired concentration of Gd-160 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Gd-160 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Gd-161 become adsorbed to the solid carbon nanostructured material. In some cases, adsorbed Gd-161 decays to generate Tb-161.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Gd-161, similar to the release of Lu-177 as described above in Example 1. Release solutions are described above. The loaded carbon nanostructured and release solution is optionally subjected to stirring, sonication, or other mechanical agitation to facilitate release of the Gd-161 from the solid carbon nanostructured material into the release solution.

The release solution is subjected to a separation to separate the solid carbon nanostructured material from the liquid containing dissolved Gd-161, such as using a centrifugation process, as described above in Example 1. Other separation processes can be used, such as a filtration process. The process achieves a specific activity of Gd-161 of from 50 GBq/mg to 9000 GBq/mg or any specific activity or subrange within this range and/or a ratio of Gd-161 to Gd-160 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 7

Production of Tb-161

Techniques for production of Tb-161 are performed using the general principles outlined in Example 1, but using various different reagents and materials. An aqueous solution including target nuclide atoms in the form of a cation, as described above in Example 1, or a molecular anion is prepared, but any suitable soluble Gd-160 salts can be used in place of ytterbium nitrate. In this Example, the Gd-160 salt is a Gd-160 nitrate salt, a Gd-160 sulfate salt, a Gd-160 phosphate salt, or a sodium, potassium, or ammonium gadolinate salt of Gd-160. The Gd-160 salt is added to the aqueous solution to achieve any desired concentration of Gd-160 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Gd-160 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Gd-161 and/or Tb-161 become adsorbed to the solid carbon nanostructured material. In some cases, adsorbed Gd-161 decays to generate Tb-161.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Tb-161, similar to the release of Lu-177 as described above in Example 1. Release solutions are described above. The loaded carbon nanostructured and release solution is optionally subjected to stirring, sonication, or other mechanical agitation to facilitate release of the Tb-161 from the solid carbon nanostructured material into the release solution.

The release solution is subjected to a separation to separate the solid carbon nanostructured material from the liquid containing dissolved Tb-161, such as using a centrifugation process, as described above in Example 1. Other separation processes can be used, such as a filtration process. The process achieves a specific activity of Tb-161 of from 50 GBq/mg to 9000 GBq/mg or any specific activity or subrange within this range and/or a ratio of Tb-161 to Gd-160 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 8

Production of Mo-99

Techniques for production of Mo-99 are performed using the general principles outlined in Example 1, but using various different reagents and materials. An aqueous solution including target nuclide atoms in the form of a cation, as described above in Example 1, or a molecular anion is prepared, but any suitable soluble Mo-98 salts can be used in place of ytterbium nitrate. In this Example, the Mo-98 salt is a Mo-98 nitrate salt, a Mo-98 sulfate salt, a Mo-98 phosphate salt, or a sodium, potassium, or ammonium molybdate salt of Mo-98. The Mo-98 salt is added to the aqueous solution to achieve any desired concentration of Mo-98 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Gd-160 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Mo-99 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Mo-99, similar to the release of Lu-177 as described above in Example 1. Release solutions are described above. The loaded carbon nanostructured and release solution is optionally subjected to stirring, sonication, or other mechanical agitation to facilitate release of the Mo-99 from the solid carbon nanostructured material into the release solution.

The release solution is subjected to a separation to separate the solid carbon nanostructured material from the liquid containing dissolved Mo-99, such as using a centrifugation process, as described above in Example 1. Other separation processes can be used, such as a filtration process. The process achieves a specific activity of Mo-99 of from 50 GBq/mg to 9000 GBq/mg or any specific activity or subrange within this range and/or a ratio of Mo-99 to Mo-98 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 9

Production of Tc-99m

Techniques for production of Tc-99m are performed using the general principles outlined in Example 1, but using various different reagents and materials. An aqueous solution including target nuclide atoms in the form of a cation, as described above in Example 1, or a molecular anion is prepared, but any suitable soluble Mo-98 salts can be used in place of ytterbium nitrate. In this Example, the Mo-98 salt is a Mo-98 nitrate salt, a Mo-98 sulfate salt, a Mo-98 phosphate salt, or a sodium, potassium, or ammonium molybdate salt of Mo-98. The Gd-160 salt is added to the aqueous solution to achieve any desired concentration of Gd-160 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Mo-98 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Mo-99 and/or Tc-99m become adsorbed to the solid carbon nanostructured material. In some cases, adsorbed Mo-99 decays to generate Tc-99m.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Tc-99m, similar to the release of Lu-177 as described above in Example 1. Release solutions are described above. The loaded carbon nanostructured and release solution is optionally subjected to stirring, sonication, or other mechanical agitation to facilitate release of the Tc-99m from the solid carbon nanostructured material into the release solution.

The release solution is subjected to a separation to separate the solid carbon nanostructured material from the liquid containing dissolved Tc-99m, such as using a centrifugation process, as described above in Example 1. Other separation processes can be used, such as a filtration process. The process achieves a specific activity of Tc-99m of from 50 GBq/mg to 9000 GBq/mg or any specific activity or subrange within this range and/or a ratio of Tc-99m to Mo-98 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 10

Production of Ho-166

Techniques for production of Ho-166 are performed using the general principles outlined in Example 1, but using various different reagents and materials. An aqueous solution including target nuclide atoms in the form of a cation, as described above in Example 1, or a molecular anion is prepared, but any suitable soluble Ho-165 salts can be used in place of ytterbium nitrate. In this Example, the Ho-165 salt is a Ho-165 nitrate salt, a Ho-165 sulfate salt, a Ho-165 phosphate salt, or a sodium, potassium, or ammonium holmate salt of Ho-165. The Ho-165 salt is added to the aqueous solution to achieve any desired concentration of Ho-165 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Ho-165 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1\times10^{13}$ neutrons/cm$^2$ to $1\times10^{20}$ neutrons/cm$^2$ or any fluence or subrange within this range. As a consequence of the irradiation process, atoms of Ho-166 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Ho-166, similar to the release of Lu-177 as described above in Example 1. Release solutions are described above. The loaded carbon nanostructured and release solution is optionally subjected to stirring, sonication, or other mechanical agitation to facilitate release of the Ho-166 from the solid carbon nanostructured material into the release solution.

The release solution is subjected to a separation to separate the solid carbon nanostructured material from the liquid containing dissolved Ho-166, such as using a centrifugation process, as described above in Example 1. Other separation processes can be used, such as a filtration process. The process achieves a specific activity of Ho-166 of from 50 GBq/mg to 9000 GBq/mg or any specific activity or subrange within this range and/or a ratio of Ho-166 to Ho-165 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 11

Production of Dy-165

Techniques for production of Dy-165 are performed using the general principles outlined in Example 1, but using various different reagents and materials. An aqueous solution including target nuclide atoms in the form of a cation, as described above in Example 1, or a molecular anion is prepared, but any suitable soluble Dy-164 salts can be used in place of ytterbium nitrate. In this Example, the Dy-164 salt is a Dy-164 nitrate salt, a Dy-164 sulfate salt, a Dy-164 phosphate salt, or a sodium, potassium, or ammonium dyprosate salt of Dy-164. The Dy-164 salt is added to the aqueous solution to achieve any desired concentration of Dy-164 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Dy-164 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1\times10^{13}$ neutrons/cm$^2$ to $1\times10^{20}$ neutrons/cm$^2$ or any fluence or subrange within this range. As a consequence of the irradiation process, atoms of Dy-165 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Dy-165, similar to the release of Lu-177 as described above in Example 1. Release solutions are described above. The loaded carbon nanostructured and release solution is optionally subjected to stirring, sonication, or other mechanical agitation to facilitate release of the Dy-165 from the solid carbon nanostructured material into the release solution.

The release solution is subjected to a separation to separate the solid carbon nanostructured material from the liquid containing dissolved Dy-165, such as using a centrifugation process, as described above in Example 1. Other separation processes can be used, such as a filtration process. The process achieves a specific activity of Dy-165 of from 50 GBq/mg to 9000 GBq/mg or any specific activity or subrange within this range and/or a ratio of Dy-165 to Dy-164 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 12

Production of Dy-166

Techniques for production of Dy-166 are performed using the general principles outlined in Example 1, but using various different reagents and materials. An aqueous solution including target nuclide atoms in the form of a cation, as described above in Example 1, or a molecular anion is prepared, but any suitable soluble Ho-165 salts can be used in place of ytterbium nitrate. In this Example, the Ho-165 salt is a Ho-165 nitrate salt, a Ho-165 sulfate salt, a Ho-165 phosphate salt, or a sodium, potassium, or ammonium holmate salt of Ho-165. The Ho-165 salt is added to the aqueous solution to achieve any desired concentration of Ho-165 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Ho-165 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Dy-166 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Dy-166, similar to the release of Lu-177 as described above in Example 1. Release solutions are described above. The loaded carbon nanostructured and release solution is optionally subjected to stirring, sonication, or other mechanical agitation to facilitate release of the Dy-166 from the solid carbon nanostructured material into the release solution.

The release solution is subjected to a separation to separate the solid carbon nanostructured material from the liquid containing dissolved Dy-166, such as using a centrifugation process, as described above in Example 1. Other separation processes can be used, such as a filtration process. The process achieves a specific activity of Dy-166 of from 50 GBq/mg to 9000 GBq/mg or any specific activity or subrange within this range and/or a ratio of Dy-166 to Ho-165 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 13

Production of Ir-192

Techniques for production of Ir-192 are performed using the general principles outlined in Example 1, but using various different reagents and materials. An aqueous solution including target nuclide atoms in the form of a cation, as described above in Example 1, or a molecular anion is prepared, but any suitable soluble Ir-191 salts can be used in place of ytterbium nitrate. In this Example, the Ir-191 salt is a Ir-191 nitrate salt, a Ir-191 sulfate salt, or a Ir-191 phosphate salt. The Ir-191 salt is added to the aqueous solution to achieve any desired concentration of Ir-191 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Ir-191 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Ir-192 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Ir-192, similar to the release of Lu-177 as described above in Example 1. Release solutions are described above. The loaded carbon nanostructured and release solution is optionally subjected to stirring, sonication, or other mechanical agitation to facilitate release of the Ir-192 from the solid carbon nanostructured material into the release solution.

The release solution is subjected to a separation to separate the solid carbon nanostructured material from the liquid containing dissolved Ir-192, such as using a centrifugation process, as described above in Example 1. Other separation processes can be used, such as a filtration process. The process achieves a specific activity of Ir-192 of from 50 GBq/mg to 9000 GBq/mg or any specific activity or subrange within this range and/or a ratio of Ir-192 to Ir-191 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 14

Production of Sn-117m

Techniques for production of Sn-117m are performed using the general principles outlined in Example 1, but using various different reagents and materials. An aqueous solution including target nuclide atoms in the form of a cation, as described above in Example 1, or a molecular anion is prepared, but any suitable soluble Sn-116 salts can be used in place of ytterbium nitrate. In this Example, the Sn-116 salt is a Sn-116 nitrate salt, a Sn-116 sulfate salt, a Sn-116 phosphate salt, or a sodium, potassium, or ammonium stannate salt of Sn-116. The Sn-116 salt is added to the aqueous solution to achieve any desired concentration of Sn-116 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Sn-116 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Sn-117m become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Sn-117m, similar to the release of Lu-177 as described above in Example 1. Release solutions are described above. The loaded carbon nanostructured and release solution is optionally subjected to stirring, sonication, or other mechanical agitation to facilitate release of the Sn-117m from the solid carbon nanostructured material into the release solution.

The release solution is subjected to a separation to separate the solid carbon nanostructured material from the liquid containing dissolved Sn-117m, such as using a centrifugation process, as described above in Example 1. Other separation processes be used, such as a filtration process. The process achieves a specific activity of Sn-117m of from 50 GBq/mg to 9000 GBq/mg or any specific activity or subrange within this range and/or a ratio of Sn-117m to Sn-116 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 15

Production of Y-90

Techniques for production of Y-90 are performed using the general principles outlined in Example 1, but using various different reagents and materials. An aqueous solution including target nuclide atoms in the form of a cation, as described above in Example 1, or a molecular anion is prepared, but any suitable soluble Y-89 salts can be used in place of ytterbium nitrate. In this Example, the Y-89 salt is a Y-89 nitrate salt, a Y-89 sulfate salt, a Y-89 phosphate salt, or a sodium, potassium, or ammonium ytterbate salt of Y-89. The Y-89 salt is added to the aqueous solution to achieve any desired concentration of Y-89 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Sn-116 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Y-90 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Y-90, similar to the release of Lu-177 as described above in Example 1. Release solutions are described above. The loaded carbon nanostructured and release solution is optionally subjected to stirring, sonication, or other mechanical agitation to facilitate release of the Y-90 from the solid carbon nanostructured material into the release solution.

The release solution is subjected to a separation to separate the solid carbon nanostructured material from the liquid containing dissolved Y-90, such as using a centrifugation process, as described above in Example 1. Other separation processes can be used, such as a filtration process. The process achieves a specific activity of Y-90 of from 50 GBq/mg to 9000 GBq/mg or any specific activity or subrange within this range and/or a ratio of Y-90 to Y-89 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 16

Production of Pd-103

Techniques for production of Pd-103 are performed using the general principles outlined in Example 1, but using various different reagents and materials. An aqueous solution including target nuclide atoms in the form of a cation, as described above in Example 1, or a molecular anion is prepared, but any suitable soluble Pd-102 salts can be used in place of ytterbium nitrate. In this Example, the Pd-102 salt is a Pd-102 nitrate salt, a Pd-102 sulfate salt, or a Pd-102 phosphate salt. The Pd-102 salt is added to the aqueous solution to achieve any desired concentration of Pd-102 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Sn-116 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Pd-103 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Pd-103, similar to the release of Lu-177 as described above in Example 1. Release solutions are described above. The loaded carbon nanostructured and release solution is optionally subjected to stirring, sonication, or other mechanical agitation to facilitate release of the Pd-103 from the solid carbon nanostructured material into the release solution.

The release solution is subjected to a separation to separate the solid carbon nanostructured material from the liquid containing dissolved Pd-103, such as using a centrifugation process, as described above in Example 1. Other separation processes can be used, such as a filtration process. The process achieves a specific activity of Pd-103 of from 50 GBq/mg to 9000 GBq/mg or any specific activity or subrange within this range and/or a ratio of Pd-103 to Pd-102 ranging from 0.1 to 800 or any ratio or subrange within this range. The skilled person, from this disclosure, can vary particular concentrations within this exemplary teaching, as well as materials and irradiation conditions used to obtain the range and subrange.

EXAMPLE 17

Production of Cr-51

Techniques for production of Cr-51 are performed using the general principles outlined in Example 1, but using various different reagents and materials. An aqueous solution including target nuclide atoms in the form of a cation, as described above in Example 1, or a molecular anion are prepared, but any suitable soluble Cr-50 salts can be used in place of ytterbium nitrate. In this Example, the Cr-50 salt is a Cr-50 nitrate salt, a Cr-50 sulfate salt, a Cr-50 phosphate salt, or a sodium, potassium, or ammonium chromate salt of Cr-50. The Cr-50 salt is added to the aqueous solution to achieve any desired concentration of Cr-50 in the solution from 0.001 mg/ml to 1 mg/ml or any concentration or subrange within this range.

A surfactant solution is prepared, as described above in Example 1, to allow for a preparation of a suspension with a suitable solid adsorber material, a solid carbon nanostructured material. Example surfactants are described above; in this Example gum arabic is used, as in Example 1. The surfactant is added to the surfactant solution to achieve any suitable concentration from 0.001 mg/ml to 300 mg/ml or any concentration or subrange within this range.

The solid carbon nanostructured material is added to the surfactant solution and agitated to prepare a suspension, as described above in Example 1. Example solid carbon nanostructured materials are described above; in this Example, single walled carbon nanotubes (SWCNT) are used, as in Example 1. The solid carbon nanostructured material is added to achieve any suitable mass ratio of the solid carbon nanostructured material to the Cr-50 in the suspension from 1:1 to 100:1 or any ratio or subrange within this range.

The suspension of the target nuclide and the solid carbon nanostructured material is placed in an irradiation vial and then irradiated with neutron radiation from a nuclear fission reactor, as described above (see earlier examples). Any suitable irradiation duration can be used from 10 minutes to 30 days or any duration or subrange within this range. The neutron radiation can have any suitable fluence from $1 \times 10^{13}$ neutrons/cm$^2$ to $1 \times 10^{20}$ neutrons/cm$^2$ or any fluence or subrange within this range. As a consequence of the irradiation process, atoms of Cr-51 become adsorbed to the solid carbon nanostructured material.

Following irradiation, the irradiation vial is retrieved, and the suspension is subjected to a separation to separate the solid carbon nanostructured material from the aqueous solution using a centrifugation process, as described above in Example 1. Other separation processes can be used, such as a filtration process. The solid phase containing loaded solid carbon nanostructured material is collected and optionally washed using deionized water one or more times to remove any residual target nuclide material and surfactant.

The loaded solid carbon nanostructured material is exposed to any suitable release solution to release the Cr-51, similar to the release of Lu-177 as described above in Example 1. Release solutions are described above. The loaded carbon nanostructured and release solution is optionally subjected to stirring, sonication, or other mechanical agitation to facilitate release of the Cr-51 from the solid carbon nanostructured material into the release solution.

The release solution is subjected to a separation to separate the solid carbon nanostructured material from the liquid containing dissolved Cr-51 using a centrifugation process, as described above in Example 1. Other separation processes can be used, such as a filtration process. The process achieves a specific activity of Cr-51 of from 50 GBq/mg to 9000 GBq/mg or any specific activity or subrange within this range and/or a ratio of Cr-51 to Cr-50 ranging from 0.1 to 800 or any ratio or subrange within this range. The skilled person, from this disclosure, can vary particular concentrations within this exemplary teaching, as well as materials and irradiation conditions used to obtain the range and subrange.

REFERENCES

U.S. Pat. No. 6,222,896.
PCT International Application Publication No. WO 2011/111010.
Bandyopadhyaya, R., Nativ-Roth, E., Regev, O., Yerushalmi-Rozen, R., 2002, Stabilization of Individual Carbon Nanotubes in Aqueous Solutions. Nano Letters, 2(1), 25-28.
Dash, A., 2015, Production of 177Lu for Targeted Radionuclide Therapy: Available Options. Nucl. Med. Mol. Imaging, 49, 85-107.
Deb, A. K. S, Pahan, S., Dasgupta, K., Panja, S., Debnath, A. K., Dhami, P. S., Ali, Sk. M., Kaushik, C. P., Yadav, J. S., 2018, Carbon Nano Tubes Functionalized with Novel Functional Group Amido-Amine for Sorption of Actinides. J. Hazardous Materials, 345, 63-75.
Fan, Q. H., Shao, D. D., Hu, J., Chen, C. L., Wu, W. S., Wang, X. K., 2009, Adsorption of Humic Acid and Eu(III) to Multi-Walled Carbon Nanotubes: Effect of pH, Ionic Strength and Counterion Effect. Radiochim. Acta, 97, 141-148.
Harbottle, G., 1965, Chemical Effects of Nuclear Transformations in Inorganic Solids. Annu. Rev. Nucl. Sci., 15, 89-124.
Horowitz, E. P., McAlister, D. R., Bond, A. H., Barrans, R. E., Williamson, J. M., 2005, A Process for the Separation of 177Lu from Neutron Irradiated 176Yb Targets. Appl. Radiat. Isot., 63(1), 23-36.
Lin, T. K., Yeh, S. J., 1966, Enrichment of Copper-64 by the Szilard Chalmers Process. J. Nucl. Sci. Technol., 3(7), 289-293.
Ramasamy, D. L., Puhakka, V., Doshi, B., Iftekhar, S., Sillanpaa, M., 2019, Fabrication of Carbon Nanotubes Reinforced Silica Composites with Improved Rare Earth Elements Adsorption Performance. Chem. Eng. Journal, 365, 291-304.
Safavi-Tehrani, L., Miller, G. E., Nilsson, M., 2015, Production of High Specific Activity Radiolanthanides for Medical Purposes Using the UC Irvine TRIGA Reactor. J. Radioanal. Nucl. Chem., 303, 1099-1103.
Sharaf El-Deen, S. E. A., Moussa, S. I., Mekawy, Z. A., Shehata, M. K. K., Sadeek, S. A., Someda, H. H., 2017, Evaluation of CNTs/MnO2 Composite for Adsorption of 60Co(II), 65Zn(II) and Cd(II) Ions from Aqueous Solutions. Radiochim. Acta, 105(1), 43-55.
Szilard, L., Chalmers, T. A., 1934, Chemical Separation of the Radioactive Element from its Bombarded Isotope in the Fermi Effect. Nature, 134, 462.
Tan, X. L., Xu, D., Chen, C. L., Wang, X. K., Hu, W. P., 2008, Adsorption and Kinetic Desorption Study of 152+154 Eu(III) on Multiwall Carbon Nanotubes from Aqueous Solution by Using Chelating Resin and XPS Methods. Radiochimica Acta., 96, 23-29.

Van Dorp, J. W. J., Mahes, D. S. Bode, P., Wolterbeek, H. T., Denkova, A. G, Serra-Crespo, P., 2018, Towards the Production of Carrier-Free 99Mo by Neutron Activation of 98Mo in Molybdenum Hexacarbonyl-Szilard-Chalmers Enrichment. Appl. Radiat. Isot., 140, 138-145.

Wang, X., Chen, C., Hu, W., Ding, A. Xu, D., Zhou, X., 2005, Sorption of 243Am(III) to Multiwall Carbon Nanotubes. Environ. Sci. Technol., 39, 2856-2860.

Wang, X., Yang, S., Shi, W., Li, J., Hayat, T., Wang, X., 2015, Different Interaction Mechanisms of Eu(III) and 243Am(III) with Carbon Nanotubes Studied by Batch, Spectroscopy Technique and Theoretical Calculation. Environ. Sci. Technol., 49, 11721-11728.

STATEMENTS REGARDING INCORPORATION BY REFERENCE AND VARIATIONS

All references identified throughout this application, for example patent documents including issued or granted patents or equivalents, patent application publications, and non-patent literature documents or other source material are hereby incorporated by reference herein in their entireties, as though individually incorporated by reference or set out in their entireties herein. All documents cited in references identified herein are also hereby incorporated by reference as if set out in their entireties herein.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example, "1, 2 and/or 3" is equivalent to "'1' or '2' or '3' or '1 and 2' or '1 and 3' or '2 and 3' or '1, 2, and 3'".

Every formulation or combination of components described or exemplified can be used to practice the invention, unless otherwise stated. Specific names of materials are intended to be exemplary, as it is known that one of ordinary skill in the art can name the same material differently. It will be appreciated that methods, device elements, starting materials, and synthetic methods other than those specifically exemplified can be employed in the practice of the invention without resorting to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method comprising:
   obtaining a target aqueous suspension comprising:
      water,
      a target nuclide material dissolved in the water,
      a surfactant, and
      a solid carbon nanostructured material suspended in the water, wherein the solid carbon nanostructured material comprises carbon nanotubes, single walled carbon nanotubes, multiwalled carbon nanotubes, one or more fullerenes, or any combination of these
   irradiating the target aqueous suspension with a neutron source, wherein at least some of the target nuclide material absorbs neutrons from the neutron source to generate radionuclides that recoil and are adsorbed by the solid carbon nanostructured material to form loaded solid carbon nanostructured material.

2. The method of claim 1, wherein the surfactant is dissolved in the water, or wherein the target nuclide material comprises a salt dissolved in the water, the salt comprising a target nuclide atom.

3. The method of claim 1, wherein the target nuclide material comprises a salt including a target nuclide atom having an atomic number from 21 to 83.

4. The method of claim 1, wherein the target nuclide material comprises a Yb-176 salt, a Re-185 salt, a perrhenate salt of Re-185, a Gd-160 salt, a Mo-98 salt, a Ho-165 salt, a Dy-164 salt, a Ir-191 salt, a Sn-116 salt, a Y-89 salt, a Pd-102 salt, or a Cr-50 salt.

5. The method of claim 1, wherein the radionuclides comprise Yb-177, Lu-177, Re-186, Gd-161, Tb-161, Mo-99, Tc-99m, Ho-166, Dy-165, Dy-166, Ir-192, Sn-117m, Y-90, Pd-103 or Cr-51.

6. The method of claim 1, wherein the radionuclides undergo β-particle emission to generate product radionuclides, wherein the product radionuclides comprise Lu-177, Tb-161, Tc-99m, Mo-99, Ho-166, Ir-192, Sn-117m, Y-90, Pd-103, or Cr-51.

7. The method of claim 1, wherein the solid carbon nanostructured material further comprises layered graphitic sheets, or graphene.

8. The method of claim 1, wherein the surfactant comprises one or more surfactants selected from the group consisting of gum arabic, bovine serum albumin, gelatin, chitosan, polysaccharides, collagen proteins, and graphene oxide.

9. The method of claim 1, including preparing the target aqueous suspension by:
dissolving the target nuclide material and the surfactant in the water; and
mixing the solid carbon nanostructured material with the water, the target nuclide material, and the surfactant to form the target aqueous suspension.

10. The method of claim 1, wherein about 49.5% or more of the radionuclides generated during the irradiating are captured in the loaded solid carbon nanostructured material.

11. The method of claim 1, wherein a concentration of the target nuclide material in the target aqueous suspension is from 0.001 mg/ml to 1 mg/ml.

12. The method of claim 1, wherein a concentration of the solid carbon nanostructured material in the target aqueous suspension is from 0.001 mg/ml to 10 mg/ml.

13. The method of claim 1, wherein a concentration of the surfactant in the target aqueous suspension is from 0.001 mg/ml to 300 mg/ml.

14. The method of claim 1, wherein a concentration of the target nuclide material in the target aqueous suspension is from 0.1 mg/ml to 1 mg/ml, wherein a concentration of the solid carbon nanostructured material in the target aqueous suspension is from 0.5 mg/ml to 10 mg/ml, or wherein a concentration of the surfactant in the target aqueous suspension is from 0.1 mg/ml to 100 mg/ml.

15. The method of claim 1, wherein a mass ratio of the solid carbon nanostructured material to the target nuclide material in the target aqueous suspension is from 10:1 to 100:1.

16. The method of claim 1, further comprising:
separating the loaded solid carbon nanostructured material; and
treating the loaded solid carbon nanostructured material with adsorbed radionuclides with an acid to release the radionuclides to solution.

17. The method of claim 16, wherein the radionuclides released to solution comprise Yb-177, Lu-177, Re-186, Gd-161, Tb-161, Mo-99, Tc-99m, Mo-99, Ho-166, Ir-192, Sn-117m, Y-90, Pd-103, or Cr-51.

18. The method of claim 16, further comprising separating the solid carbon nanostructured material from the solution.

19. The method of claim 16, wherein the solution has a specific activity from 50 GBq/mg to 9000 GBq/mg.

20. The method of claim 16, wherein a ratio of the radionuclides to stable or longer-lived nuclides of the target nuclide material in the solution is from 0.1 to 800.

* * * * *